US008920417B2

(12) United States Patent
Conley et al.

(10) Patent No.: US 8,920,417 B2
(45) Date of Patent: Dec. 30, 2014

(54) ELECTROSURGICAL DEVICES AND METHODS OF USE THEREOF

(71) Applicant: Medtronic Advanced Energy LLC, Minneapolis, MN (US)

(72) Inventors: Brian M. Conley, South Berwick, ME (US); Jonathan J. Barry, Stratham, NH (US); Roger D. Greeley, Portsmouth, NH (US); Chad M. Greenlaw, Somersworth, NH (US); Lorenzo C. Vaccarella, Newmarket, NH (US); Joseph Sylvester, Minneapolis, MN (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 0 days.

(21) Appl. No.: 13/729,337

(22) Filed: Dec. 28, 2012

(65) Prior Publication Data
US 2014/0039493 A1 Feb. 6, 2014

Related U.S. Application Data

(63) Continuation-in-part of application No. PCT/US2011/042356, filed on Jun. 29, 2011, which is a continuation-in-part of application No. 12/827,734, filed on Jun. 30, 2010.

(51) Int. Cl.
*A61B 18/14* (2006.01)
*A61B 18/00* (2006.01)
*A61B 17/3203* (2006.01)

(52) U.S. Cl.
CPC .............. *A61B 18/00* (2013.01); *A61B 18/149* (2013.01); *A61B 17/3203* (2013.01); *A61B 2018/00029* (2013.01); *A61B 2018/1407* (2013.01); *A61B 2018/1472* (2013.01); *A61B 2218/002* (2013.01)
USPC .................. 606/41; 606/48; 606/50

(58) Field of Classification Search
CPC .................. A61B 18/149; A61B 2018/1407; A61B 2018/144
USPC .......................... 606/32, 41, 48, 50
See application file for complete search history.

(56) References Cited

U.S. PATENT DOCUMENTS 2,888,928 A 6/1959 Seiger
3,682,130 A 8/1972 Jeffers
(Continued)

FOREIGN PATENT DOCUMENTS

DE 43 32 898 A1 3/1995
WO WO96/04955 A2 2/1996
(Continued)

OTHER PUBLICATIONS

Mulier, S., et al., "Electrodes and Multiple Electrode Systems for Radio Frequency Ablation: A Proposal for Updated Terminology," Liver & Pancreatic Diseases Management 574:57-73, Springer (2006).
(Continued)

Primary Examiner — Linda Dvorak
Assistant Examiner — Jocelyn D Ram
(74) Attorney, Agent, or Firm — Jeffrey J. Hohenshell

(57) ABSTRACT

In some embodiments, an electrosurgical device includes a shaft, a first U-shaped electrode at a distal end of the shaft, and a second blade shaped electrode at the distal end of the shaft. The second electrode includes a spherical distal end. And the second electrode is substantially coplanar with the first electrode such that the first electrode surrounds a perimeter of the second electrode. The second electrode is spaced from the first electrode by an aperture. In some embodiments, an electrosurgical device includes a shaft, a first electrode at a distal end of the shaft defining an aperture and comprising a pointed tip, and a second electrode disposed at the distal end of the shaft that is substantially coplanar with the first electrode such that the first electrode surrounds a perimeter of the second electrode. The second electrode is spaced from the first electrode by the aperture.

15 Claims, 30 Drawing Sheets

(56) References Cited

U.S. PATENT DOCUMENTS

| | | |
|---|---|---|
| 3,750,650 A | 8/1973 | Ruttgers |
| 4,060,088 A | 11/1977 | Morrison, Jr. et al. |
| 4,195,637 A | 4/1980 | Gruntzig et al. |
| 4,207,897 A | 6/1980 | Lloyd et al. |
| 4,244,371 A | 1/1981 | Farin |
| 4,248,224 A | 2/1981 | Jones |
| 4,275,734 A | 6/1981 | Mitchiner |
| 4,276,874 A | 7/1981 | Wolvek et al. |
| 4,278,090 A | 7/1981 | van Gerven |
| 4,321,931 A | 3/1982 | Hon |
| 4,342,218 A | 8/1982 | Fox |
| 4,355,642 A | 10/1982 | Alferness |
| 4,377,168 A | 3/1983 | Rzasa et al. |
| 4,381,007 A | 4/1983 | Doss |
| 4,519,389 A | 5/1985 | Gudkin et al. |
| 4,598,698 A | 7/1986 | Siegmund |
| 4,601,290 A | 7/1986 | Effron et al. |
| 4,671,274 A | 6/1987 | Scrochenko |
| 4,736,749 A | 4/1988 | Lundback |
| 4,779,611 A | 10/1988 | Grooters et al. |
| 4,919,129 A | 4/1990 | Weber et al. |
| 4,931,047 A | 6/1990 | Broadwin et al. |
| 4,932,952 A | 6/1990 | Wojciechowicz, Jr. |
| 4,943,290 A | 7/1990 | Rexroth et al. |
| 4,950,232 A | 8/1990 | Ruzicka et al. |
| 4,985,030 A | 1/1991 | Melzer et al. |
| 4,998,933 A | 3/1991 | Eggers et al. |
| 5,047,028 A | 9/1991 | Qian |
| 5,190,541 A | 3/1993 | Abele et al. |
| 5,195,959 A | 3/1993 | Smith |
| 5,197,964 A | 3/1993 | Parins |
| 5,254,117 A | 10/1993 | Rigby et al. |
| 5,281,215 A | 1/1994 | Milder |
| 5,287,845 A | 2/1994 | Faul et al. |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,330,521 A | 7/1994 | Cohen |
| 5,334,181 A | 8/1994 | Rubinsky et al. |
| 5,334,193 A | 8/1994 | Nardella |
| 5,336,220 A | 8/1994 | Ryan et al. |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,383,874 A | 1/1995 | Jackson et al. |
| 5,385,148 A | 1/1995 | Lesh et al. |
| 5,395,312 A | 3/1995 | Desai |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,401,272 A | 3/1995 | Perkins |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,417,709 A | 5/1995 | Slater |
| 5,423,807 A | 6/1995 | Milder |
| 5,423,811 A | 6/1995 | Imran et al. |
| 5,427,119 A | 6/1995 | Swartz et al. |
| 5,431,168 A | 7/1995 | Webster, Jr. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,441,503 A | 8/1995 | Considine et al. |
| 5,443,463 A | 8/1995 | Stern et al. |
| 5,443,470 A | 8/1995 | Stern et al. |
| 5,445,638 A | 8/1995 | Rydell et al. |
| 5,450,843 A | 9/1995 | Moll et al. |
| 5,452,582 A | 9/1995 | Longsworth |
| 5,452,733 A | 9/1995 | Sterman et al. |
| 5,460,629 A | 10/1995 | Shlain et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,490,819 A | 2/1996 | Nicholas et al. |
| 5,496,271 A | 3/1996 | Burton et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,700 A | 4/1996 | Leone |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,540,679 A | 7/1996 | Fram et al. |
| 5,542,196 A | 8/1996 | Kantro |
| 5,542,945 A | 8/1996 | Fritzsch |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,556,397 A | 9/1996 | Long et al. |
| 5,558,671 A | 9/1996 | Yates |
| 5,560,362 A | 10/1996 | Silwa, Jr. et al. |
| 5,562,720 A | 10/1996 | Stern et al. |
| 5,569,241 A | 10/1996 | Edwards |
| 5,569,243 A | 10/1996 | Kortenbach et al. |
| 5,571,088 A | 11/1996 | Lennox et al. |
| 5,571,215 A | 11/1996 | Sterman et al. |
| 5,573,424 A | 11/1996 | Poppe |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,599,346 A | 2/1997 | Edwards et al. |
| 5,607,422 A | 3/1997 | Smeets et al. |
| 5,607,462 A | 3/1997 | Imran |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,647,869 A | 7/1997 | Goble et al. |
| 5,656,029 A | 8/1997 | Imran et al. |
| 5,658,278 A | 8/1997 | Imran et al. |
| 5,658,280 A | 8/1997 | Issa |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |
| 5,681,278 A | 10/1997 | Igo et al. |
| 5,681,294 A | 10/1997 | Osborne et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |

(56) References Cited

U.S. PATENT DOCUMENTS

| | | | |
|---|---|---|---|
| 5,697,927 | A | 12/1997 | Imran et al. |
| 5,697,928 | A | 12/1997 | Walcott et al. |
| 5,713,942 | A | 2/1998 | Stern |
| 5,716,389 | A | 2/1998 | Walinsky et al. |
| 5,718,241 | A | 2/1998 | Ben-Haim et al. |
| 5,718,701 | A | 2/1998 | Shai et al. |
| 5,720,775 | A | 2/1998 | Larnard |
| 5,722,402 | A | 3/1998 | Swanson et al. |
| 5,730,074 | A | 3/1998 | Peter |
| 5,730,127 | A | 3/1998 | Avitall |
| 5,730,704 | A | 3/1998 | Avitall |
| 5,733,280 | A | 3/1998 | Avitall |
| 5,735,280 | A | 4/1998 | Sherman et al. |
| 5,735,290 | A | 4/1998 | Sterman et al. |
| 5,743,903 | A | 4/1998 | Stern et al. |
| 5,746,224 | A | 5/1998 | Edwards et al. |
| 5,755,760 | A | 5/1998 | Maguire et al. |
| 5,766,171 | A | 6/1998 | Silvestrini |
| 5,769,846 | A | 6/1998 | Edwards et al. |
| 5,782,828 | A | 7/1998 | Chen et al. |
| 5,785,706 | A | 7/1998 | Bednarek |
| 5,788,636 | A | 8/1998 | Curley |
| 5,792,140 | A | 8/1998 | Tu et al. |
| 5,797,905 | A | 8/1998 | Fleischman et al. |
| 5,797,960 | A | 8/1998 | Stevens et al. |
| 5,800,428 | A | 9/1998 | Nelson et al. |
| 5,800,482 | A | 9/1998 | Pomeranz et al. |
| 5,810,764 | A | 9/1998 | Eggers et al. |
| 5,810,802 | A | 9/1998 | Panescu et al. |
| 5,827,216 | A | 10/1998 | Igo et al. |
| 5,836,947 | A | 11/1998 | Fleischman et al. |
| 5,840,030 | A | 11/1998 | Ferek-Petric et al. |
| 5,843,021 | A | 12/1998 | Edwards et al. |
| 5,843,152 | A | 12/1998 | Tu et al. |
| 5,844,349 | A | 12/1998 | Oakley et al. |
| 5,846,187 | A | 12/1998 | Wells et al. |
| 5,846,191 | A | 12/1998 | Wells et al. |
| 5,849,028 | A | 12/1998 | Chen |
| 5,855,061 | A * | 1/1999 | Malis et al. ............ 606/50 |
| 5,861,021 | A | 1/1999 | Thome et al. |
| 5,871,523 | A | 2/1999 | Fleischman et al. |
| 5,871,525 | A | 2/1999 | Edwards et al. |
| 5,873,845 | A | 2/1999 | Cline et al. |
| 5,873,855 | A | 2/1999 | Eggers et al. |
| 5,876,399 | A | 3/1999 | Chia et al. |
| 5,879,295 | A | 3/1999 | Li et al. |
| 5,879,296 | A | 3/1999 | Ockuly et al. |
| 5,879,348 | A | 3/1999 | Owens et al. |
| 5,881,732 | A | 3/1999 | Sung et al. |
| 5,882,346 | A | 3/1999 | Pomeranz et al. |
| 5,885,278 | A | 3/1999 | Fleischman |
| 5,891,142 | A | 4/1999 | Eggers et al. |
| 5,893,848 | A | 4/1999 | Negus et al. |
| 5,895,355 | A | 4/1999 | Schaer |
| 5,895,417 | A | 4/1999 | Pomeranz et al. |
| 5,897,553 | A | 4/1999 | Mulier et al. |
| 5,897,554 | A | 4/1999 | Chia et al. |
| 5,899,898 | A | 5/1999 | Arless et al. |
| 5,899,899 | A | 5/1999 | Arless et al. |
| 5,902,289 | A | 5/1999 | Swartz et al. |
| 5,904,711 | A | 5/1999 | Flom et al. |
| 5,906,580 | A | 5/1999 | Kline-Schoder et al. |
| 5,906,587 | A | 5/1999 | Zimmon |
| 5,906,606 | A | 5/1999 | Chee et al. |
| 5,908,029 | A | 6/1999 | Knudson et al. |
| 5,913,854 | A | 6/1999 | Maguire et al. |
| 5,916,213 | A | 6/1999 | Haissaguerre et al. |
| 5,916,214 | A | 6/1999 | Cosio et al. |
| 5,921,924 | A | 7/1999 | Avitall |
| 5,921,982 | A | 7/1999 | Lesh et al. |
| 5,925,045 | A | 7/1999 | Reimels et al. |
| 5,927,284 | A | 7/1999 | Borst et al. |
| 5,928,191 | A | 7/1999 | Houser et al. |
| 5,931,810 | A | 8/1999 | Grabek |
| 5,931,848 | A | 8/1999 | Saadat |
| 5,935,123 | A | 8/1999 | Edwards et al. |
| 5,935,125 | A * | 8/1999 | Zupkas ............ 606/46 |
| 5,944,715 | A | 8/1999 | Goble et al. |
| 5,954,661 | A | 9/1999 | Greenspon et al. |
| 5,957,919 | A | 9/1999 | Laufer et al. |
| 5,971,980 | A | 10/1999 | Sherman |
| 5,971,983 | A | 10/1999 | Lesh |
| 5,976,129 | A | 11/1999 | Desai |
| 5,980,516 | A | 11/1999 | Mulier et al. |
| 5,980,519 | A | 11/1999 | Hahnen et al. |
| 5,989,248 | A | 11/1999 | Tu et al. |
| 5,993,412 | A | 11/1999 | Deily et al. |
| 5,993,445 | A | 11/1999 | Issa |
| 5,993,447 | A | 11/1999 | Blewett et al. |
| 6,004,316 | A | 12/1999 | Laufer |
| 6,004,319 | A | 12/1999 | Goble et al. |
| 6,007,499 | A | 12/1999 | Martin et al. |
| 6,010,500 | A | 1/2000 | Sherman et al. |
| 6,012,457 | A | 1/2000 | Lesh |
| 6,015,391 | A | 1/2000 | Rishton et al. |
| 6,016,811 | A | 1/2000 | Knopp et al. |
| 6,018,676 | A | 1/2000 | Davis et al. |
| 6,019,757 | A | 2/2000 | Scheldrup |
| 6,024,733 | A | 2/2000 | Eggers et al. |
| 6,030,381 | A | 2/2000 | Jones et al. |
| 6,036,687 | A | 3/2000 | Laufer et al. |
| 6,042,556 | A | 3/2000 | Beach et al. |
| 6,048,333 | A | 4/2000 | Lennox et al. |
| 6,056,744 | A | 5/2000 | Edwards |
| 6,056,745 | A | 5/2000 | Panescu et al. |
| 6,056,746 | A | 5/2000 | Goble |
| 6,056,747 | A | 5/2000 | Saadat et al. |
| 6,063,081 | A | 5/2000 | Mulier |
| 6,066,139 | A | 5/2000 | Ryan et al. |
| 6,068,653 | A | 5/2000 | LaFontaine |
| 6,071,279 | A | 6/2000 | Whayne et al. |
| 6,071,283 | A * | 6/2000 | Nardella et al. ............ 606/46 |
| 6,080,152 | A * | 6/2000 | Nardella et al. ............ 606/46 |
| 6,083,237 | A | 7/2000 | Huitema et al. |
| 6,086,585 | A | 7/2000 | Hovda et al. |
| 6,088,894 | A | 7/2000 | Oakley |
| 6,096,037 | A | 8/2000 | Mulier |
| 6,113,592 | A | 9/2000 | Taylor |
| 6,113,596 | A | 9/2000 | Hooven et al. |
| 6,117,101 | A | 9/2000 | Diederich et al. |
| 6,120,496 | A | 9/2000 | Whayne et al. |
| 6,141,576 | A | 10/2000 | Littmann et al. |
| 6,142,993 | A | 11/2000 | Whayne et al. |
| 6,142,994 | A | 11/2000 | Swanson et al. |
| 6,149,620 | A | 11/2000 | Baker et al. |
| 6,152,920 | A | 11/2000 | Thompson et al. |
| 6,161,543 | A | 12/2000 | Cox et al. |
| 6,165,174 | A | 12/2000 | Jacobs et al. |
| 6,190,384 | B1 | 2/2001 | Ouchi |
| 6,193,716 | B1 | 2/2001 | Shannon, Jr. |
| 6,210,406 | B1 | 4/2001 | Webster |
| 6,210,410 | B1 | 4/2001 | Farin et al. |
| 6,210,411 | B1 | 4/2001 | Hofmann et al. |
| 6,212,426 | B1 | 4/2001 | Swanson |
| 6,216,704 | B1 | 4/2001 | Ingle et al. |
| 6,217,528 | B1 | 4/2001 | Koblish et al. |
| 6,217,575 | B1 | 4/2001 | DeVore et al. |
| 6,217,576 | B1 | 4/2001 | Tu et al. |
| 6,224,592 | B1 | 5/2001 | Eggers et al. |
| 6,231,518 | B1 | 5/2001 | Grabek et al. |
| 6,231,591 | B1 | 5/2001 | Desai |
| 6,235,020 | B1 | 5/2001 | Cheng et al. |
| 6,235,024 | B1 | 5/2001 | Tu |
| 6,237,605 | B1 | 5/2001 | Vaska et al. |
| 6,238,347 | B1 | 5/2001 | Nix et al. |
| 6,238,387 | B1 | 5/2001 | Miller, III |
| 6,238,391 | B1 * | 5/2001 | Olsen et al. ............ 606/41 |
| 6,238,393 | B1 | 5/2001 | Mulier |
| 6,245,061 | B1 | 6/2001 | Panescu et al. |
| 6,245,064 | B1 | 6/2001 | Lesh et al. |
| 6,245,065 | B1 | 6/2001 | Panescu et al. |
| 6,251,092 | B1 | 6/2001 | Qin et al. |
| 6,251,110 | B1 | 6/2001 | Wampler |
| 6,251,128 | B1 | 6/2001 | Knopp et al. |

(56) References Cited

U.S. PATENT DOCUMENTS

| | | |
|---|---|---|
| 6,258,087 B1 | 7/2001 | Edwards et al. |
| 6,264,650 B1 | 7/2001 | Hovda et al. |
| 6,266,551 B1 | 7/2001 | Osadchy et al. |
| 6,270,471 B1 | 8/2001 | Hechel et al. |
| 6,283,988 B1 | 9/2001 | Laufer et al. |
| 6,283,989 B1 | 9/2001 | Laufer et al. |
| 6,293,943 B1 | 9/2001 | Panescu et al. |
| 6,296,619 B1 | 10/2001 | Brisken et al. |
| 6,299,633 B1 | 10/2001 | Laufer |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,322,559 B1 | 11/2001 | Daulton et al. |
| 6,325,797 B1 | 12/2001 | Stewart et al. |
| 6,328,735 B1 | 12/2001 | Curley et al. |
| 6,328,736 B1 | 12/2001 | Mulier |
| 6,332,881 B1 | 12/2001 | Carner et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,371,956 B1 | 4/2002 | Wilson et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,416,509 B1 | 7/2002 | Goble et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,478,793 B1 | 11/2002 | Cosman et al. |
| 6,484,727 B1 | 11/2002 | Vaska et al. |
| 6,488,678 B2 | 12/2002 | Sherman |
| 6,488,680 B1 | 12/2002 | Francischelli |
| 6,497,704 B2 | 12/2002 | Ein-Gal |
| 6,502,575 B1 | 1/2003 | Jacobs et al. |
| 6,508,815 B1 | 1/2003 | Strul et al. |
| 6,514,250 B1 | 2/2003 | Jahns |
| 6,517,536 B2 | 2/2003 | Hooven et al. |
| 6,527,767 B2 | 3/2003 | Wang et al. |
| 6,537,248 B2 | 3/2003 | Mulier |
| 6,558,382 B2 | 5/2003 | Jahns |
| 6,558,385 B1 | 5/2003 | McClurken et al. |
| 6,575,969 B1 | 6/2003 | Rittman, III et al. |
| 6,579,288 B1 | 6/2003 | Swanson et al. |
| 6,584,360 B2 | 6/2003 | Francischelli |
| 6,585,732 B2 | 7/2003 | Mulier |
| 6,602,248 B1 | 8/2003 | Sharps et al. |
| 6,603,988 B2 | 8/2003 | Dowlatshahi |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,635,034 B1 | 10/2003 | Cosmescu |
| 6,645,199 B1 | 11/2003 | Jenkins et al. |
| 6,645,202 B1 | 11/2003 | Pless et al. |
| 6,648,883 B2 | 11/2003 | Francischelli |
| 6,656,175 B2 | 12/2003 | Francischelli |
| 6,663,627 B2 | 12/2003 | Francischelli |
| 6,666,862 B2 | 12/2003 | Jain et al. |
| 6,679,882 B1 | 1/2004 | Kornerup |
| 6,682,501 B1 | 1/2004 | Nelson |
| 6,689,131 B2 | 2/2004 | McClurken |
| 6,692,450 B1 | 2/2004 | Coleman |
| 6,699,240 B2 | 3/2004 | Francischelli |
| 6,702,810 B2 | 3/2004 | McClurken et al. |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,766,202 B2 | 7/2004 | Underwood et al. |
| 6,766,817 B2 | 7/2004 | da Silva |
| 6,773,433 B2 | 8/2004 | Stewart et al. |
| 6,775,575 B2 | 8/2004 | Bommannan et al. |
| 6,776,780 B2 | 8/2004 | Mulier |
| 6,786,906 B1 | 9/2004 | Cobb |
| 6,807,968 B2 | 10/2004 | Francischelli |
| 6,827,713 B2 | 12/2004 | Bek et al. |
| 6,827,715 B2 | 12/2004 | Francischelli |
| 6,832,996 B2 | 12/2004 | Woloszko et al. |
| 6,849,073 B2 | 2/2005 | Hoey |
| 6,858,028 B2 | 2/2005 | Mulier |
| 6,887,238 B2 | 5/2005 | Jahns et al. |
| 6,899,711 B2 | 5/2005 | Stewart et al. |
| 6,911,019 B2 | 6/2005 | Mulier |
| 6,915,806 B2 | 7/2005 | Pacek et al. |
| 6,916,318 B2 | 7/2005 | Francischelli |
| 6,918,404 B2 | 7/2005 | Dias da Silva |
| 6,936,046 B2 | 8/2005 | Hissong |
| 6,942,661 B2 | 9/2005 | Swanson |
| 6,949,097 B2 | 9/2005 | Stewart et al. |
| 6,949,098 B2 | 9/2005 | Mulier |
| 6,953,461 B2 | 10/2005 | McClurken et al. |
| 6,960,205 B2 | 11/2005 | Jahns |
| 6,962,589 B2 | 11/2005 | Mulier |
| 6,986,767 B2 | 1/2006 | Durgin et al. |
| 6,991,631 B2 | 1/2006 | Woloszko et al. |
| 7,066,586 B2 | 6/2006 | da Silva |
| 7,156,845 B2 | 1/2007 | Mulier et al. |
| 7,166,105 B2 | 1/2007 | Mulier et al. |
| 7,207,471 B2 | 4/2007 | Heinrich et al. |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,309,325 B2 | 12/2007 | Mulier et al. |
| 7,311,708 B2 | 12/2007 | McClurken |
| 7,361,175 B2 | 4/2008 | Suslov |
| 7,364,579 B2 | 4/2008 | Mulier et al. |
| 7,422,588 B2 | 9/2008 | Mulier et al. |
| 7,537,595 B2 | 5/2009 | McClurken |
| RE40,863 E | 7/2009 | Tay et al. |
| 7,604,635 B2 | 10/2009 | McClurken et al. |
| 7,608,072 B2 | 10/2009 | Swanson |
| 7,645,277 B2 | 1/2010 | McClurken et al. |
| 7,651,494 B2 | 1/2010 | McClurken et al. |
| 7,678,108 B2 | 3/2010 | Chrisitian et al. |
| 7,691,050 B2 | 4/2010 | Gellman |
| 7,704,249 B2 | 4/2010 | Woloszko et al. |
| 7,736,361 B2 | 6/2010 | Palanker |
| 7,811,282 B2 | 10/2010 | McClurken |
| 7,815,634 B2 | 10/2010 | McClurken et al. |
| 7,909,820 B2 | 3/2011 | Lipson |
| 7,942,872 B2 | 5/2011 | Ein-Gal |
| 7,976,544 B2 | 7/2011 | McClurken |
| 7,993,337 B2 | 8/2011 | Lesh |
| 7,997,278 B2 | 8/2011 | Utley et al. |
| 7,998,140 B2 | 8/2011 | McClurken |
| 8,034,071 B2 | 10/2011 | Scribner et al. |
| 8,038,670 B2 | 10/2011 | McClurken |
| 8,048,070 B2 | 11/2011 | O'Brien |
| 8,083,736 B2 | 12/2011 | Mcclurken et al. |
| 8,105,323 B2 | 1/2012 | Buysse et al. |
| 8,172,828 B2 | 5/2012 | Chang et al. |
| 8,177,783 B2 | 5/2012 | Davison et al. |
| 8,216,233 B2 | 7/2012 | McClurken |
| 8,323,276 B2 | 12/2012 | Palanker et al. |

(56) References Cited

U.S. PATENT DOCUMENTS

| | | |
|---|---|---|
| 8,348,946 B2 | 1/2013 | McClurken |
| 8,361,068 B2 | 1/2013 | McClurken |
| 8,388,642 B2 | 3/2013 | Muni et al. |
| 8,414,572 B2 | 4/2013 | Davison et al. |
| 8,475,455 B2 | 7/2013 | McClurken |
| 2001/0025177 A1* | 9/2001 | Woloszko et al. ............ 606/41 |
| 2001/0032002 A1 | 10/2001 | McClurken et al. |
| 2002/0049483 A1 | 4/2002 | Knowlton |
| 2002/0062131 A1 | 5/2002 | Gallo, Sr. |
| 2002/0082643 A1 | 6/2002 | Milla et al. |
| 2002/0161363 A1 | 10/2002 | Fodor et al. |
| 2003/0009164 A1 | 1/2003 | Woloszko et al. |
| 2003/0014050 A1 | 1/2003 | Sharkey et al. |
| 2003/0032954 A1 | 2/2003 | Carranza et al. |
| 2003/0045872 A1 | 3/2003 | Jacobs |
| 2003/0073993 A1 | 4/2003 | Ciarrocca |
| 2003/0144656 A1 | 7/2003 | Ocel |
| 2003/0191462 A1 | 10/2003 | Jacobs |
| 2003/0204185 A1 | 10/2003 | Sherman et al. |
| 2003/0216724 A1 | 11/2003 | Jahns |
| 2004/0015106 A1 | 1/2004 | Coleman |
| 2004/0015219 A1 | 1/2004 | Francischelli |
| 2004/0024395 A1 | 2/2004 | Ellman et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0111136 A1 | 6/2004 | Sharkey et al. |
| 2004/0111137 A1 | 6/2004 | Sharkey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0090816 A1 | 4/2005 | McClurken et al. |
| 2005/0143729 A1 | 6/2005 | Francischelli |
| 2005/0165392 A1 | 7/2005 | Francischelli |
| 2005/0171525 A1 | 8/2005 | Rioux |
| 2005/0209564 A1 | 9/2005 | Bonner |
| 2005/0251134 A1* | 11/2005 | Woloszko et al. ............ 606/46 |
| 2005/0267454 A1 | 12/2005 | Hissong |
| 2005/0273097 A1 | 12/2005 | Ryan |
| 2006/0009756 A1 | 1/2006 | Francischelli |
| 2006/0009759 A1 | 1/2006 | Christian |
| 2006/0064085 A1 | 3/2006 | Schechter et al. |
| 2006/0106375 A1 | 5/2006 | Werneth et al. |
| 2006/0111709 A1 | 5/2006 | Goble et al. |
| 2006/0149225 A1 | 7/2006 | McClurken |
| 2007/0049920 A1 | 3/2007 | McClurken et al. |
| 2007/0093808 A1 | 4/2007 | Mulier et al. |
| 2007/0118114 A1 | 5/2007 | Miller et al. |
| 2007/0149965 A1 | 6/2007 | Gallo, Sr. et al. |
| 2007/0208332 A1 | 9/2007 | Mulier et al. |
| 2008/0015563 A1 | 1/2008 | Hoey et al. |
| 2008/0058796 A1 | 3/2008 | O'Brien et al. |
| 2008/0071270 A1 | 3/2008 | Desinger et al. |
| 2008/0103494 A1 | 5/2008 | Rioux |
| 2008/0207028 A1 | 8/2008 | Schutz |
| 2008/0262489 A1 | 10/2008 | Steinke |
| 2008/0275439 A1 | 11/2008 | Francischelli et al. |
| 2009/0264879 A1 | 10/2009 | McClurken et al. |
| 2009/0306655 A1 | 12/2009 | Stangenes et al. |
| 2010/0016854 A1 | 1/2010 | Carmel et al. |
| 2010/0023007 A1* | 1/2010 | Sartor et al. ............ 606/49 |
| 2010/0069904 A1 | 3/2010 | Cunningham |
| 2010/0160906 A1 | 6/2010 | Jarrard |
| 2010/0204560 A1 | 8/2010 | Salahieh et al. |
| 2010/0241178 A1 | 9/2010 | Tilson et al. |
| 2010/0274178 A1 | 10/2010 | LePivert et al. |
| 2011/0028965 A1 | 2/2011 | McClurken |
| 2011/0137298 A1 | 6/2011 | Nguyen et al. |
| 2011/0178515 A1 | 7/2011 | Bloom et al. |
| 2011/0196367 A1 | 8/2011 | Gallo |
| 2011/0295249 A1 | 12/2011 | Bloom et al. |
| 2011/0319889 A1 | 12/2011 | Conley et al. |
| 2012/0004657 A1 | 1/2012 | Conley et al. |
| 2012/0071712 A1 | 3/2012 | Manwaring et al. |
| 2012/0095461 A1 | 4/2012 | Herscher et al. |
| 2012/0101496 A1 | 4/2012 | McClurken et al. |
| 2012/0116397 A1 | 5/2012 | Rencher et al. |
| 2012/0143293 A1 | 6/2012 | Mauch et al. |
| 2012/0150165 A1 | 6/2012 | Conley et al. |
| 2012/0157989 A1 | 6/2012 | Stone et al. |
| 2012/0184983 A1 | 7/2012 | Chang et al. |
| 2012/0191084 A1 | 7/2012 | Davison et al. |
| 2012/0232553 A1 | 9/2012 | Bloom et al. |
| 2012/0253343 A1 | 10/2012 | McClurken et al. |

FOREIGN PATENT DOCUMENTS

| | | |
|---|---|---|
| WO | WO 97/40759 A1 | 11/1997 |
| WO | WO2007-037785 | 4/2007 |
| WO | WO 2010/000697 A1 | 1/2010 |
| WO | WO 2010/120944 A2 | 10/2010 |
| WO | WO2010/141417 | 12/2010 |

OTHER PUBLICATIONS

Aubry-Frize, M., and Poussart, Y., "Modelling of thermal patterns of electrosurgical dispersive electrodes," *Medical & Biological Engineering & Computing* 24:311-16 (2006).

Lee, J. et al., "Hepatic Radiofrequency Ablation Using Multiple Probes: Ex Vivo and In Vivo Comparative Studies of Monopolar versus Multipolar Modes," *Korean J. Radiol.* 7(2):106-17 (2006).

Shellock, F., "Radiofrequency energy induced heating of bovine articular cartilage: comparison between temperature-controlled, monopolar, and bipolar systems," *Knee Surg., Sports Traumatol, Arthrosc.* 9:392-97, Springer-Verlag (2001).

Shuman, I.E., "Bipolar Versus Monopolar Electrosurgery: Clinical Applications," *Dentistry Today* 20(12), 7 pages, (2001).

International Search Report and Written Opinion for International Appl. No. PCT/US2011/042356, European Patent Office, The Netherlands, mailed on Mar. 11, 2011, 12 pages.

\* cited by examiner

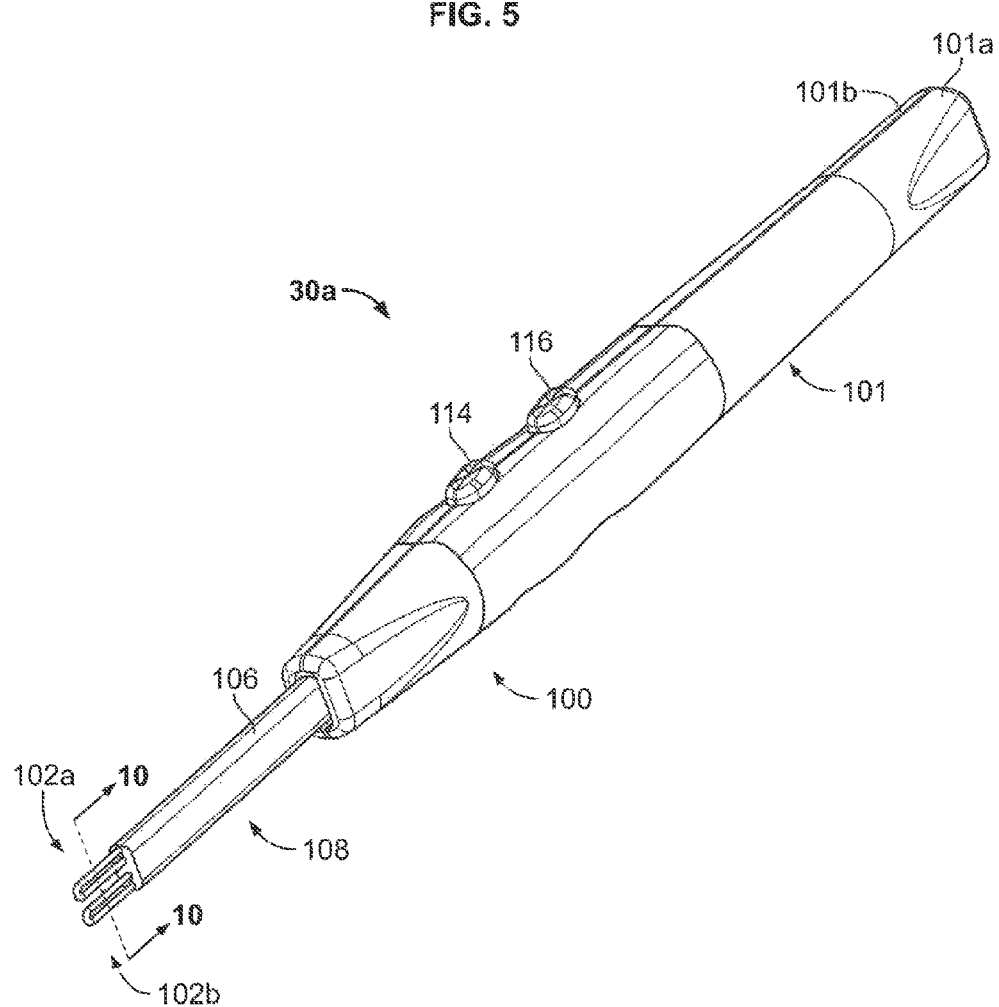

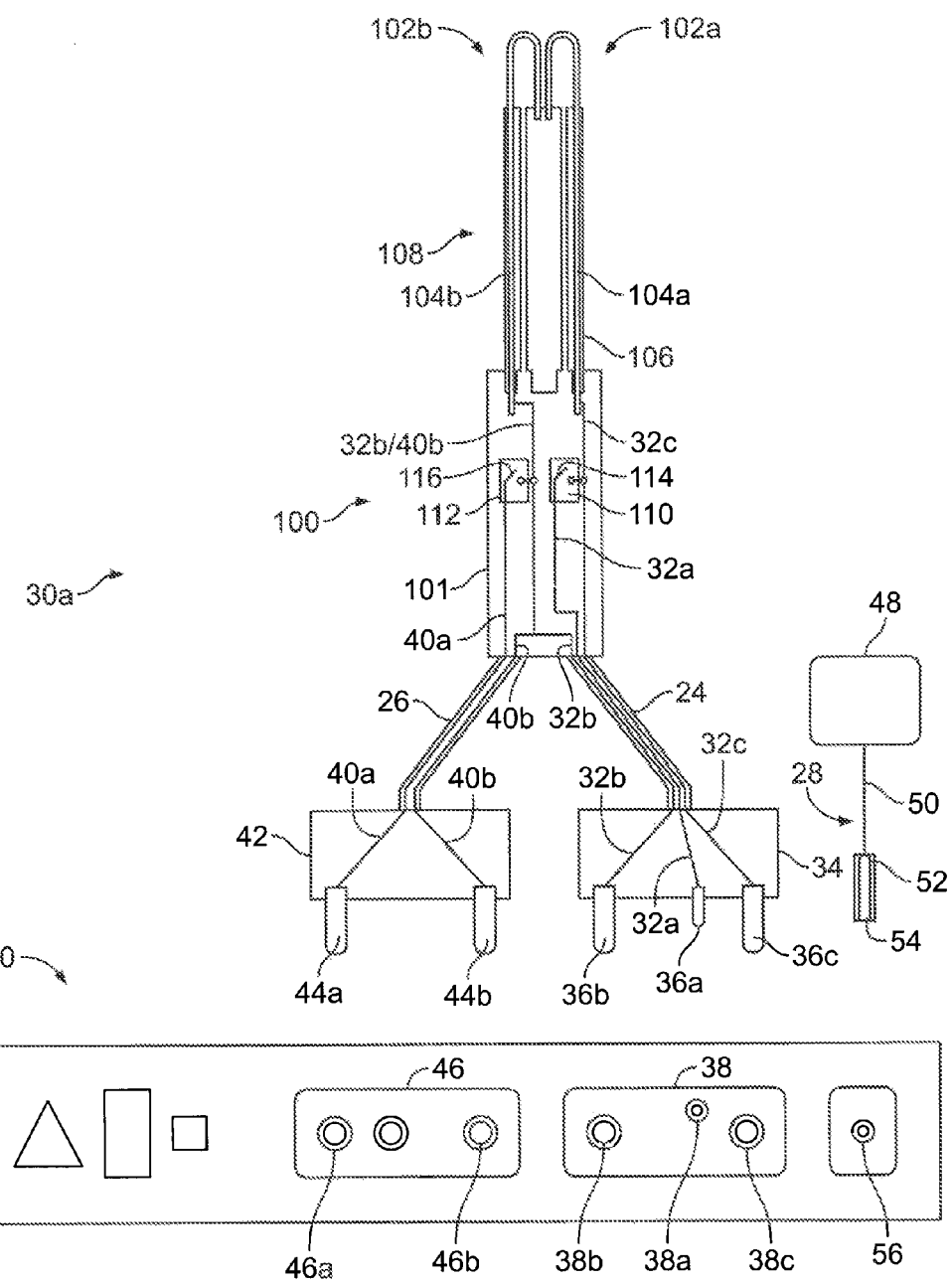

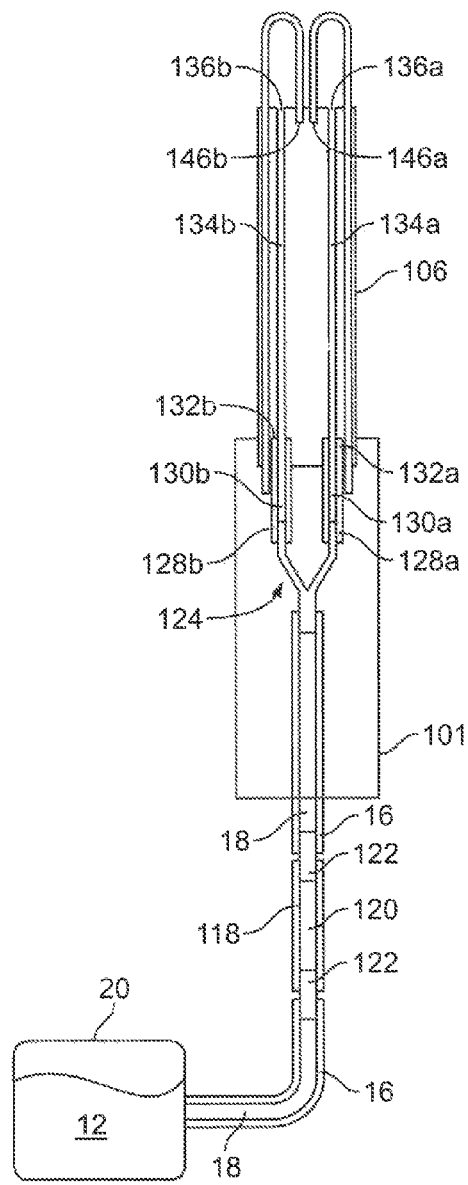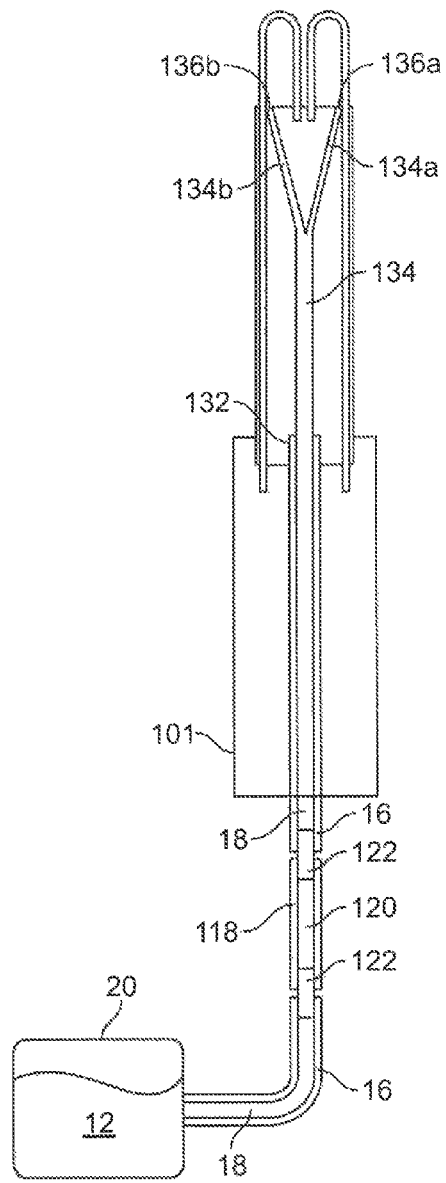

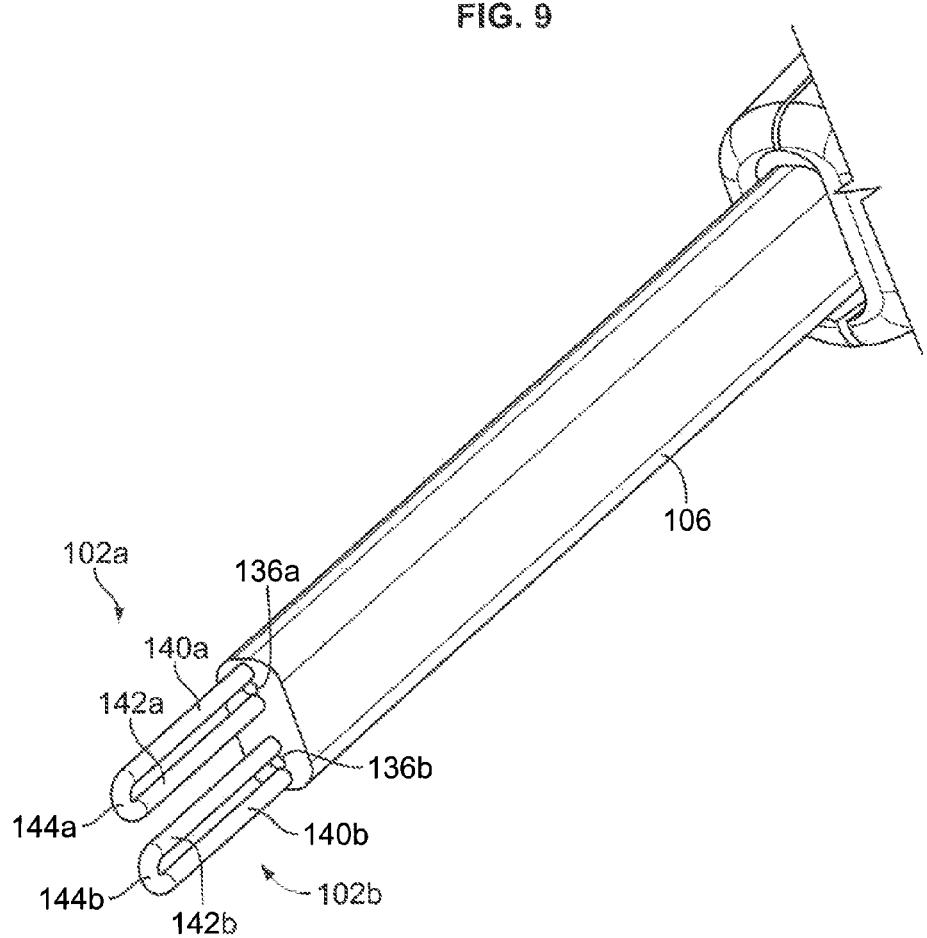

ELECTROSURGICAL DEVICES AND METHODS OF USE THEREOF

CROSS REFERENCE TO RELATED APPLICATIONS

This application is a continuation-in-part of International Application No. PCT/US2011/042356, filed Jun. 29, 2011, which claims the benefit of U.S. application Ser. No. 12/827,734, filed Jun. 30, 2010. Each of the above referenced applications is incorporated by reference in its entirety.

BACKGROUND OF THE INVENTION

1. Field of the Invention

Embodiments of this invention relate generally to the field of medical devices, systems, and methods for use upon a human body during surgery. More particularly, embodiments of this invention relate to electrosurgical devices, systems, and methods for cutting tissue and for coagulation, hemostasis, and sealing of tissue to inhibit blood and other fluid loss during surgery such as abdominal, orthopedic, head, spine and thoracic surgery as well as general surgery of the body.

2. Background Art

Fluid-assisted electrosurgical devices have been developed which, when used in conjunction with an electrically conductive fluid such as saline, may be moved along a tissue surface, without cutting the tissue, to seal tissue to inhibit blood and other fluid loss during surgery. However, to cut tissue the surgeon must utilize a second device, which necessitates delays associated when switching between devices. What is still needed is an electrosurgical device which is capable of cutting tissue as well as providing fluid-assisted sealing of tissue to inhibit blood and other fluid loss during surgery, as well as inhibit undesirable effects of tissue desiccation, tissue sticking to the electrode, tissue perforation, char formation, and smoke generation. What is also needed is an electrosurgical device which cuts tissue with reduced lateral thermal spread and damage to adjacent tissue.

BRIEF SUMMARY OF THE INVENTION

In some embodiments, an electrosurgical device includes a shaft, a first U-shaped electrode at a distal end of the shaft, and a second blade shaped electrode at the distal end of the shaft. The second electrode includes a spherical distal end and is substantially coplanar with the first electrode such that the first electrode surrounds a perimeter of the second electrode. The second electrode is spaced from the first electrode by an aperture.

In some embodiments, an electrosurgical device includes a shaft, a first electrode at a distal end of the shaft. The first electrode defines an aperture and comprises a pointed tip. The electrosurgical device further comprises a second electrode disposed at the distal end of the shaft that is substantially coplanar with the first electrode such that the first electrode surrounds a perimeter of the second electrode. The second electrode is spaced from the first electrode by the aperture.

In some embodiments, an electrosurgical device can treat tissue with fluid from a fluid source and radio-frequency power from a radio-frequency power source. Particularly, the electrosurgical device can provide a bipolar power output and a monopolar power output. The device may comprise a distal portion comprising a first electrode tip, a second electrode tip, and at least one fluid outlet. The first and second electrode tips may be configured as bipolar electrodes that receive the bipolar power output from the radio-frequency power source to treat tissue, particularly, by moving along a tissue surface in the presence of a bipolar power output and a fluid provided simultaneously from the distal portion. At least one of the electrode tips may be configured as a monopolar electrode that receives the monopolar power output from the radio-frequency power source and that provides an electrosurgical cutting edge for cutting tissue by moving along a tissue surface in the presence of monopolar power output provided from the distal portion.

In certain embodiments, the electrosurgical device may comprise a handle, a shaft distal to the handle, a first electrode tip and a second electrode tip adjacent a distal end of the shaft, with the first electrode tip spaced from the second electrode tip and wherein the first electrode tip comprises a first wire electrode having a U-shape and the second electrode tip comprises a second wire electrode having a U-shape, and at least one fluid outlet.

Each of the first and second U-shape electrodes may comprise an arcuate distal segment and two longitudinal segments extending distally relative to a distal end of the shaft. The arcuate distal segment of each of the first and second U-shape electrodes may be arcuate from one longitudinal segment to the other longitudinal segment, and may be semicircular between the two longitudinal segments. At least one of the U-shape electrodes may provide a cutting edge, which may be an electrosurgical cutting edge and may be arranged along a longitudinal length of the U-shape electrode. The cutting edge may particularly be straight (linear).

The first electrode and a second electrode may be formed from metal wire. The metal wire may be single stand (solid core) wire, and more particularly circular single strand wire. The metal wire may be stainless steel wire. In this manner, the electrodes may have a low mass, which may allow the electrodes to dissipate heat and cool quickly during and after tissue treatment, which may inhibit damage to adjacent tissue (not to be treated) due to lateral thermal spread.

The at least one fluid outlet may be located a distal end of the shaft. More particularly, the fluid outlet may be located between the two longitudinal segments of at least one of the U-shape electrodes.

The at least one fluid outlet may comprise a first fluid outlet and second fluid outlet. The first fluid outlet may be located between the two longitudinal segments of the first U-shape electrode, and the second fluid outlet is located between the two longitudinal segments of the second U-shape electrode.

The U-shape electrodes may be coplanar. The two longitudinal segments of the first U-shape electrode and the two longitudinal segments of the second U-shape electrode may be parallel, and more particularly in a single plane.

One longitudinal segment of each of the first and second U-shape electrodes may be a medial longitudinal segment and the other longitudinal segment may be a lateral longitudinal segment.

The two longitudinal segments of the second U-shape electrode may be medial relative to the two longitudinal segments of the first U-shape electrode.

The first U-shape electrode may surround a perimeter of the second U-shape electrode, and the second U-shape electrode may be located within a U-shape aperture defined by the first U-shape electrode.

Each of the first and second U-shape electrodes may comprise an arcuate distal segment, and the arcuate distal end segments may be concentric.

The first U-shape electrode and the second U-shape electrode may have at least one of a same size and a same shape, and a position of first U-shape electrode and a position of the second U-shape electrode may be fixed relative to one another.

In certain embodiments, the electrosurgical device may comprise a handle, a shaft distal to the handle, a first electrode tip and a second electrode tip adjacent a distal end of the shaft, with the first electrode tip spaced from the second electrode tip and wherein the first electrode tip comprises a first electrode having a first arcuate wire portion forming an arc of at least 180 degrees and the second electrode tip comprises a second electrode having a second arcuate wire portion forming an arc of at least 180 degrees, and at least one fluid outlet.

In certain embodiments, the electrosurgical device may comprise a handle, a shaft distal to the handle, and a first electrode and a second electrode adjacent a distal end of the shaft with the first electrode coplanar with the second electrode and comprising a wire electrode having a U-shape which surrounds a perimeter of the second electrode and is spaced from the second electrode by an aperture. In certain embodiments, the second electrode may comprise a wire electrode having a linear segment, a U-shape or a blade shaped member. The device may also comprise at least one fluid outlet.

BRIEF DESCRIPTION OF THE DRAWINGS

FIG. 5 is a perspective view of an electrosurgical device according to the present invention;

FIG. 6 is a plan view showing the various electrical connections and conductors of the device of FIG. 5 with the electrosurgical unit of FIG. 1;

FIG. 7 is a plan view showing a first embodiment of the various fluid connections and passages of the device of FIG. 5 with the electrosurgical unit and fluid source of FIG. 1;

FIG. 8 is a plan view showing a second embodiment of the fluid connections and passages of the device of FIG. 5 with the electrosurgical unit and fluid source of FIG. 1;

FIG. 9 is a close-up view of the shaft of the device of FIG. 5;

DETAILED DESCRIPTION OF THE INVENTION

Figure 1:
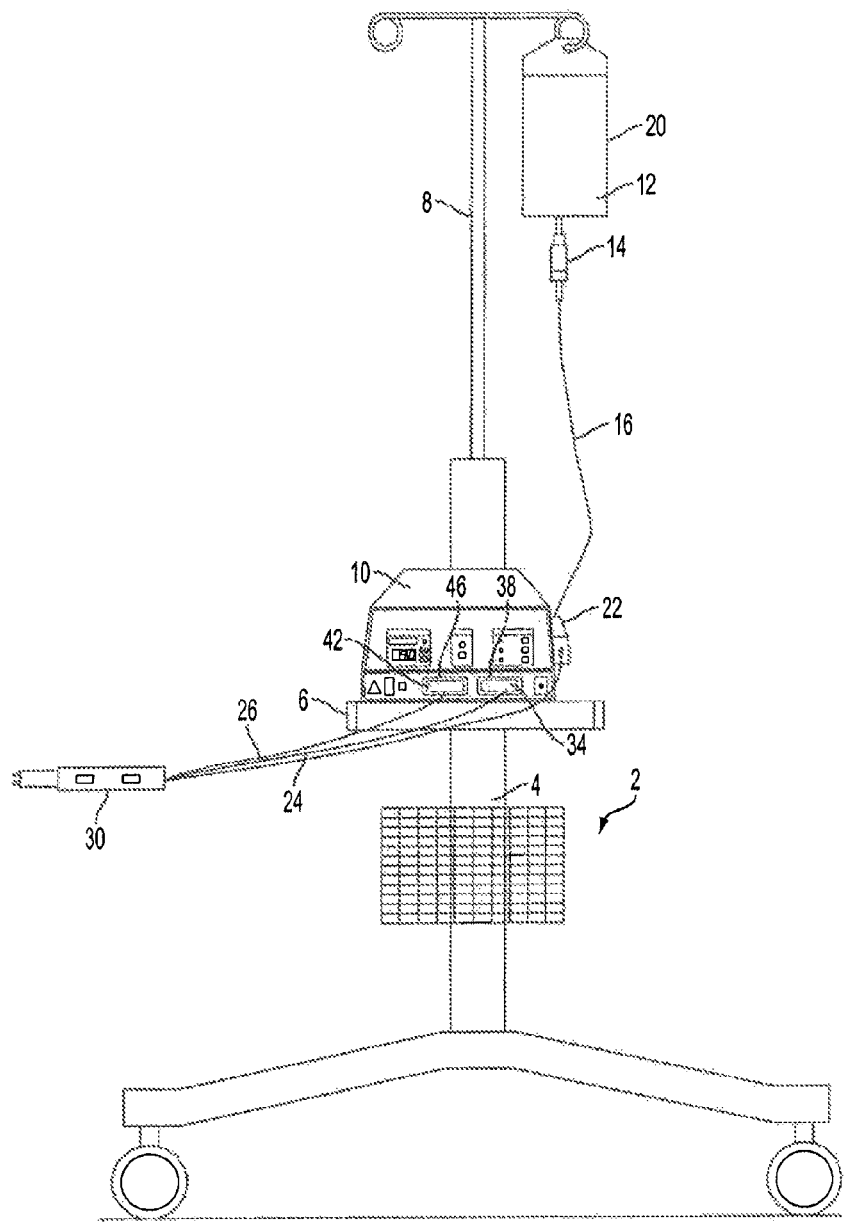
FIG. 1 is a front view of one embodiment of a system of the present invention having an electrosurgical unit in combination with a fluid source and handheld electrosurgical device.

Throughout the description, like reference numerals and letters indicate corresponding structure throughout the several views. Also, any particular feature(s) of a particular exemplary embodiment may be equally applied to any other exemplary embodiment(s) of this specification as suitable. In other words, features between the various exemplary embodiments described herein are interchangeable as suitable, and not exclusive. Prom the specification, it should be clear that any use of the terms "distal" and "proximal" are made in reference to the user of the device, and not the patient.

Embodiments of the invention comprise systems, devices, and methods to control tissue temperature at a tissue treatment site during an electrosurgical procedure, as well as shrinking, coagulating, cutting, and sealing tissue against blood and other fluid loss, for example, by shrinking the lumens of blood vessels (e.g., arteries or veins). In some embodiments, the devices may be configured, due to the narrow electrode size, to fit through a trocar down to a size as small as 5 mm.

Embodiments of the invention will now be discussed with reference to the figures, with FIG. 1 showing a front view of one embodiment of a system of the present invention which may include an electrosurgical unit 10 in combination with a fluid source 20 and a handheld electrosurgical device 30. In addition, FIG. 1 shows a movable cart 2 having a support member 4 comprising a hollow cylindrical post which carries a platform 6 comprising a pedestal table to provide a flat, stable surface for supporting the electrosurgical unit 10.

As shown, cart 2 further comprises a fluid source carrying pole 8 having a height which may be adjusted by sliding the carrying pole 8 up and down within the support member 4 and thereafter secured in position with a set screw. On the top of the fluid source carrying pole 8 is a cross support provided with loops at the ends thereof to provide a hook for carrying fluid source 20.

As shown in FIG. 1, fluid source 20 may comprise a bag of fluid from which fluid 12 may flow through a drip chamber 14, particularly after the bag is penetrated with a spike located at the end of the drip chamber 14. Thereafter, fluid 12 may flow through flexible and compressible fluid delivery tubing 16 to handheld electrosurgical device 30. The fluid delivery tubing 16 may be made from a synthetic polymer material, such as polyvinyl chloride.

As shown in FIG. 1, the fluid delivery tubing 16 passes through pump 22. As shown, pump 22 may comprise a peristaltic pump and, more specifically, a rotary peristaltic pump. With a rotary peristaltic pump, a portion of the delivery tubing 16 may be loaded into the pump head by raising and lowering the pump head in a known manner. Fluid 12 may then be conveyed within the delivery tubing 16 by waves of contraction placed externally on the tubing 16 which may be produced mechanically, typically by rotating pinch rollers which rotate on a drive shaft and intermittently compress the tubing 16 against an anvil support, Peristaltic pumps may be particularly used, as the electro-mechanical force mechanism, here rollers driven by electric motor, do not contact the fluid 12, thus reducing the likelihood of inadvertent contamination.

In the present embodiment the fluid 12 may particularly comprise liquid saline solution, and even more particularly, normal (0.9% w/v NaCl or physiologic) saline. Although the description herein may make reference to saline as the fluid 12, other electrically conductive fluids may be used in accordance with the invention.

Additionally, while an electrically conductive fluid having an electrically conductivity similar to normal saline may be preferred, as will become more apparent with further reading of this specification, fluid 12 may also be an electrically non-conductive fluid. The use of a non-conductive fluid, while not providing all the advantage of an electrically conductive fluid, still provides certain advantages over the use of a dry electrode including, for example, reduced occurrence of tissue sticking to the electrode of device 30 and cooling of the electrode and/or tissue. Therefore, it is also within the scope of the invention to include the use of an electrically non-conductive fluid, such as, for example, deionized water.

Electrosurgical unit 10 may be configured to provide both monopolar and bipolar radio-frequency (RF) power output. However, electrosurgical unit 10 may particularly include a lock out feature which prevents both monopolar and bipolar output from being activated simultaneously. Alternatively, rather than use a single electrosurgical unit 10, device 30 may be simultaneously connected to two separate electrosurgical units. For example, device 30 may be connected to a first electrosurgical unit 10 to provide monopolar power output thereto and a second electrosurgical unit 10 to provide bipolar power output thereto.

During monopolar operation of electrosurgical device 30, a first electrode, often referred to as the active electrode, may be provided with electrosurgical device 30 while a second electrode, often referred to as the indifferent or neutral electrode, may be provided in the form of a ground pad dispersive electrode located on the patient (also known as a patient return electrode), typically on the back or other suitable anatomical location. An electrical circuit may then be formed between the active electrode and ground pad dispersive electrode with electrical current flowing from the active electrode through the patient to ground pad dispersive electrode in a manner known in the art.

During bipolar operation of electrosurgical device 30, the ground pad electrode located on the patient is not required, and a second electrode providing a second electrical pole may be provided as part of the device. An alternating current electrical circuit may then be created between the first and second electrical poles of the device. Consequently, alternating current no longer flows through the patient's body to the ground pad electrode, but rather through a localized portion of tissue between the poles of device 30. As indicated above, monopolar and bipolar power may be provided from electrosurgical unit 10 as known in the art, or from separate electrosurgical units.

As shown in FIG. 1, electrosurgical device 30 may be connected to electrosurgical unit 10 via electrical cables 24 and 26. Cable 24 is shown with a plug 34 which connects to bipolar output receptacle 38 of electro surgical unit 10, while cable 26 is shown with a plug 42 which connects to the monopolar output receptacle 46 of electrosurgical unit 10. Briefly turning to FIG. 6, when electrosurgical unit 10 is used in monopolar mode, additional cable 28 may connect a ground pad dispersive electrode 48 to the ground pad receptacle 56 of the electrosurgical unit 10.

Figure 2:
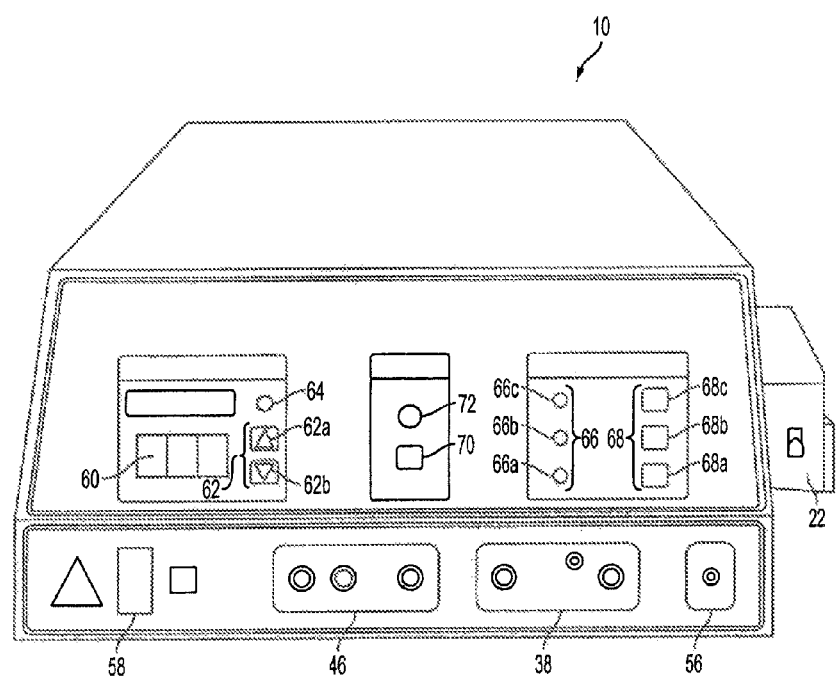
FIG. 2 is a front perspective view of the electrosurgical unit of FIG. 1.

FIG. 2 shows the front panel of exemplary electrosurgical unit 10. A power switch 58 may be used to turn the electrosurgical unit 10 on and off. After turning the electrosurgical unit 10 on, an RF power setting display 60 may be used to display the RF power setting numerically in watts. The power setting display 60 may further comprise a liquid crystal display (LCD).

Electrosurgical unit 10 may further include an RF power selector 62 comprising RF power setting switches 62a, 62b which may be used to select the RF power setting. Pushing the switch 62a may increase the RF power setting, while pushing the switch 62b may decrease the RF power setting. Electrosurgical unit 10 may also include an RF power activation display 64 comprising an indicator light which may illuminate when RF power is activated, either via a handswitch on device 30 or a footswitch. Switches 62a, 62b may comprise membrane switches. It should be understood that while only one RF power selector 62 is shown, electrosurgical unit 10 may have two such RF power selectors with one each for monopolar and bipolar power selection.

In addition to having a RF power setting display 60, electrosurgical unit 10 may further include a fluid flow rate setting display 66. Flow rate setting display 66 may comprise three indicator lights 66a, 66b, and 66c with first light 66a corresponding to a fluid flow rate setting of low, second light 66b corresponding to a fluid flow rate setting of medium (intermediate), and third light 66c corresponding to a flow rate setting of high. One of these three indicator lights will illuminate when a fluid flow rate setting is selected.

Electrosurgical unit 10 may further include a fluid flow selector 68 comprising flow rate setting switches 68a, 68b, and 68c used to select or switch the flow rate setting. Three push switches may be provided with first switch 68a corresponding to the fluid flow rate setting of low, second switch 68b corresponding to a fluid flow rate setting of medium (intermediate), and third switch 68c corresponding to a flow rate setting of high. Pushing one of these three switches may select the corresponding flow rate setting of either low, medium (intermediate), or high. The medium, or intermediate, flow rate setting may be automatically selected as the default setting if no setting is manually selected. Switches 68a, 68b and 68c may comprise membrane switches.

Before starting a surgical procedure, it may be desirable to prime device 30 with fluid 12. Priming may be desirable to inhibit RF power activation without the presence of fluid 12. A priming switch 70 may be used to initiate priming of device 30 with fluid 12. Pushing switch 70 once may initiate operation of pump 22 for a predetermined time period to prime device 30. After the time period is complete, the pump 22 may shut off automatically. When priming of device 30 is initiated, a priming display 72 comprising an indicator light may illuminate during the priming cycle.

Figure 3:
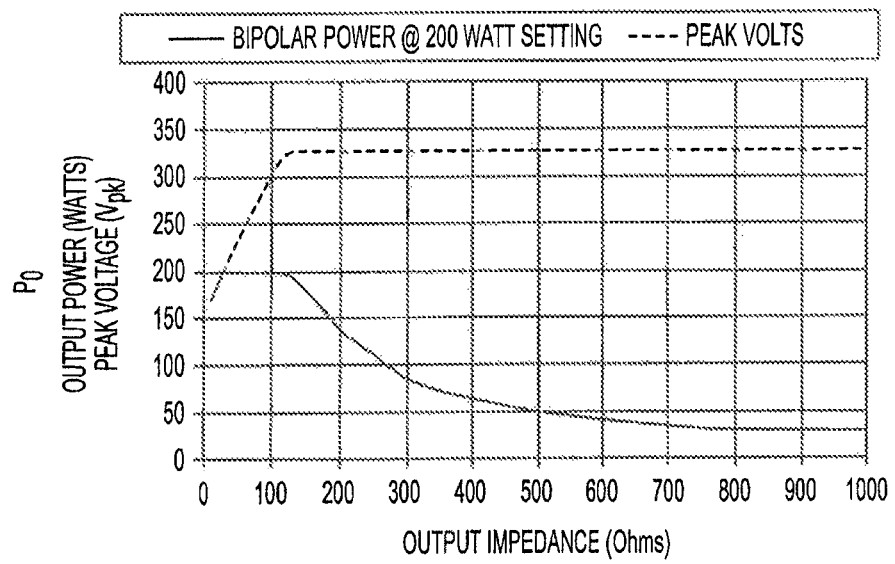
FIG. 3 is a graph of the bipolar RF power output versus impedance for the electrosurgical unit of FIG. 1.

An exemplary bipolar RF power output curve of electrosurgical unit 10 is shown in FIG. 3. Impedance Z is shown in units of ohms on the X-axis, and output power $P_O$ is shown in units of watts on the Y-axis. In the illustrated embodiment, the bipolar electrosurgical power (RF) is set to 200 watts. As shown in the figure, for an RF power setting $P_S$ of 200 watts, the output power $P_O$ will remain constant with the set RF power $P_S$ as long as the impedance Z stays between the low impedance cut-off of 30 ohms and the high impedance cut-off of 120 ohms. Below an impedance Z of 30 ohms, the output power $P_O$ will decrease as shown by the low impedance ramp. Above an impedance Z of 120 ohms, the output power $P_O$ will also decrease as shown by the high impedance ramp. With respect to monopolar power output, an exemplary monopolar RF power output curve would include that of the Valleylab Force FX, either for cut or coagulation mode, hereby incorporated by reference.

Figure 4:
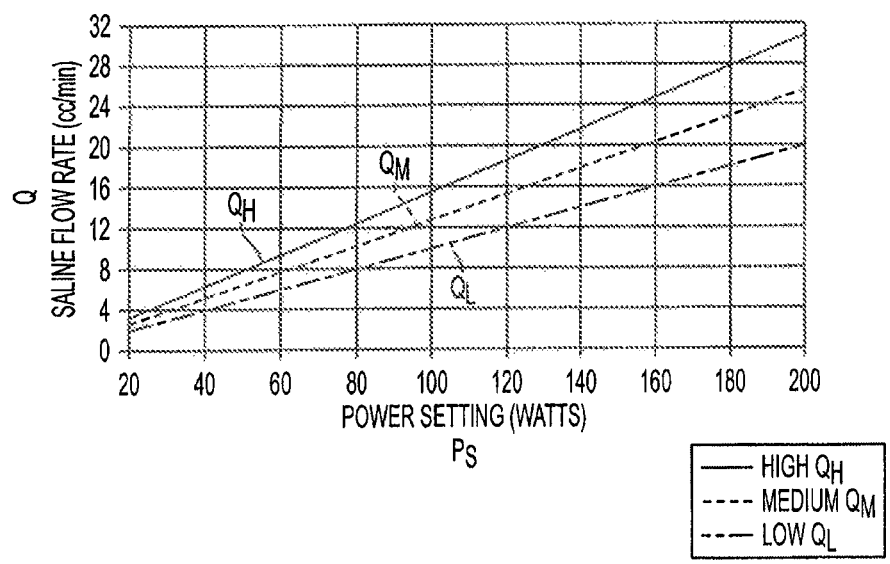
FIG. 4 is graph showing a relationship of fluid flow rate Q in units of cubic centimetres per minute (cc/min) on the Y-axis, and the RF power setting Ps in units of watts on the X-axis.

Electrosurgical unit 10 may be configured such that the speed of pump 22, and therefore the throughput of fluid 12 expelled by the pump 22, is predetermined based on two input variables, the RF power setting and the fluid flow rate setting. In FIG. 4, there is shown an exemplary functional relationship of fluid flow rate Q in units of cubic centimeters per minute (cc/min) on the Y-axis, and the RF power setting Ps in units of watts on the X-axis. The relationship may be engineered to inhibit undesirable effects such as tissue desiccation, electrode sticking, smoke production, and char formation, while at the same time not providing a fluid flow rate Q at a corresponding RF power setting Ps which is so great as to provide too much electrical dispersion and cooling at the electrode/tissue interface. While not being bound to a particular theory, a more detailed discussion on how the fluid flow rate interacts with the radio frequency power, modes of heat transfer away from the tissue, fractional boiling of the fluid, and various control strategies may be found in U.S. Publication No. 2001/0032002, published Oct. 18, 2001, which is hereby incorporated by reference in its entirety to the extent it is consistent.

As shown in FIG. 4, electrosurgical unit 10 has been configured to increase the fluid flow rate Q linearly with an increasing RF power setting Ps for each of three fluid flow rate settings of low, medium and high corresponding to $Q_L$, $Q_M$ and $Q_H$, respectively. Conversely, electrosurgical unit 10 has been configured to decrease the fluid flow rate Q linearly with a decreasing RF power setting Ps for each of three fluid flow rate settings of low, medium, and high corresponding to $Q_L$, $Q_M$, and $Q_H$, respectively.

An electrosurgical unit similar to exemplary electrosurgical unit 10 that has detailed schematic drawings, albeit without monopolar output, may be found in U.S. Publication No. 2006/0149225, published Jul. 6, 2006, which is hereby incorporated by reference in its entirety to the extent it is consistent.

While electrosurgical unit 10 as shown above includes an attached pump 22, in other embodiments pump 22 may not be integrated with electrosurgical unit 10, but rather be separate from electrosurgical unit 10.

In still other embodiments, pump 22 may be eliminated and there may be no preset functional relationship of fluid flow rate Q versus RF power setting $P_S$ stored in the electrosurgical unit 10. In such an instance, rather than the fluid flow rate Q being automatically controlled by the electrosurgical unit 10 based on the RF power setting $P_S$, the fluid flow rate Q may be manually controlled, such as by the user of device 10 or another member of the surgical team, with a roller (pinch) clamp or other clamp provided with device 10 and configured to act upon and compress the tubing 16 and control flow in a manner known in the art. Exemplary fluid flow control mechanisms may be found in U.S. Publication No. 2005/0090816, published Apr. 28, 2005, which is hereby incorporated by reference in its entirety to the extent it is consistent. An example of an electrosurgical unit which does not include a pump, but may be used in conjunction with a manually operated fluid flow control mechanism on device 10, includes an electrosurgical unit such as the Valleylab Force FX.

An exemplary bipolar and/or monopolar electrosurgical device of the present invention which may be used in conjunction with electrosurgical unit 10 of the present invention is shown at reference character 30a in FIG. 5. While various electrosurgical devices of the present invention are described herein with reference to use with electrosurgical unit 10, it should be understood that the description of the combination is for purposes of illustrating systems according to embodiments of the invention. Consequently, it should be understood that while the electrosurgical devices disclosed herein may be disclosed for use with electrosurgical unit 10, it may be plausible to use other electrosurgical devices with electrosurgical unit 10, or it may be plausible to use the electrosurgical devices disclosed herein with another electrosurgical unit.

As shown in FIG. 5, exemplary device 30a includes an elongated handpiece 100 with a handle 101 comprising mating handle portions 101a, 101b. Handpiece 100 may be configured to enable a user of device 30a to hold and manipulate device 30a between the thumb and index finger like a writing instrument. Handle 101 may comprise a sterilizable, rigid, electrically insulative material, such as a synthetic polymer (e.g., polycarbonate, acrylonitrile-butadiene-styrene).

As shown in FIG. 6, device 30a can further include cables 24 and 26, which are also shown in FIG. 1, that are connectable to electrosurgical unit 10 to provide device 30a with bipolar and monopolar power output, respectively, from electrosurgical unit 10. As further shown in FIG. 6, cable 24 of device 30a may comprise three insulated wire conductors 32a, 32b, 32c connectable to bipolar power output receptacles 38a, 38b, 38c of electrosurgical unit 10 via three banana (male) plug connectors 36a, 36b, 36c. The banana plug connectors 36a, 36b, 36c may be each assembled with insulated wire conductors 32a, 32b, 32c within the housing of plug 34 in a known manner. On device 30a, insulated wire conductor 32a may be connected to a bipolar hand switch assembly 110, and insulated wire conductors 32b, 32c may be connected to a proximal portion of electrodes 102a, 102b, particularly by welding.

Electrodes 102a, 102b thereafter may extend through linear conduits provided by cylindrical through passages 104a, 104b of elongated, rigid, electrically insulative shaft 108 comprising shaft body 106. Shaft body 106 may comprise a sterilizable, rigid, electrically insulative material, such as a synthetic polymer (e.g., polycarbonate, acrylonitrile-butadiene-styrene). At the distal end of device 30, a distal portion of electrodes 102a, 102b having a U-shape loop extends from the passages 104a, 104b of elongated shaft body 106.

Cable 26 of device 30a may comprise two insulated wire conductors 40a, 40b connectable to monopolar power output receptacles 46a, 46b of electrosurgical unit 10 via two banana (male) plug connectors 44a, 44b. The banana plug connectors 44a, 44b may be each assembled with insulated wire conductors 40a, 40b within the housing of plug 42 in a known manner. On device 30a, insulated wire conductor 40a may be connected to a monopolar hand switch assembly 112, and insulated wire conductor 40b may be connected to a proximal portion of electrode 102b of shaft 108. As shown wire conductors 32b and 40b may merge inside handle 100 and share the same attachment location to electrode 102b.

When device 30a is used in monopolar mode, an additional cable 28 may be utilized to connect a ground pad dispersive electrode 48, which is attached to the patient, to the electrosurgical unit 10 comprising wire conductor 50 and plug 52 at the end thereof having plug connector 54 which connects to the ground pad receptacle 56.

Hand switch assemblies 110 and 112 may comprise push buttons 114 and 116, respectively, which overlie domed switches on a platform comprising a printed circuit board, with the construction and wiring of the hand switch assemblies 110 and 112 known in the art. Upon depression of push buttons 114 or 116, a domed switch beneath the push button forms a closed circuit which is sensed by electrosurgical unit 10, which then provides bipolar or monopolar power, respectively. Exemplary hand switches may be found in U.S. Publication No. 2006/0149225, published Jul. 6, 2006, and U.S. Publication No. 2005/0090816, published Apr. 28, 2005, which are hereby incorporated by reference in their entirety to the extent they are consistent.

As shown FIG. 7, during use of device 30a, fluid 12 from fluid source 20 may be communicated through a tubular fluid passage provided by various structures. In the present embodiment, fluid 12 from the fluid source 20 is first communicated through lumen 18 of delivery tubing 16. Fluid 12 may then flow through lumen 120 of a special pump tubing segment 118 configured to operate specifically with the peristaltic pump 22, which may be spliced in between portions of delivery tubing 16 and connected thereto using barbed fluid line connectors 122 at each end thereof.

Within handle 101 of device 30a, fluid delivery tubing 16 may be connected to the inlet branch of a Y-splitter 124, which thereafter provides two outlet branches which may be connected to the proximal end portion of delivery tubing segments 128a, 128b. A distal end portion of the delivery tubing segments 128a, 128b may be connected to shaft body 106 by being inserted into cylindrical receptacles 132a, 132b (counter bores) of shaft body 106. Fluid 12 then may flow through lumens 130a, 130b of delivery tubing segments 128a, 128b and into tubular passages 134a, 134b formed in, shaft body 106, Fluid 12 may then be expelled from fluid delivery outlets 136a, 136b at the distal end of shaft body 106.

Figure 10:
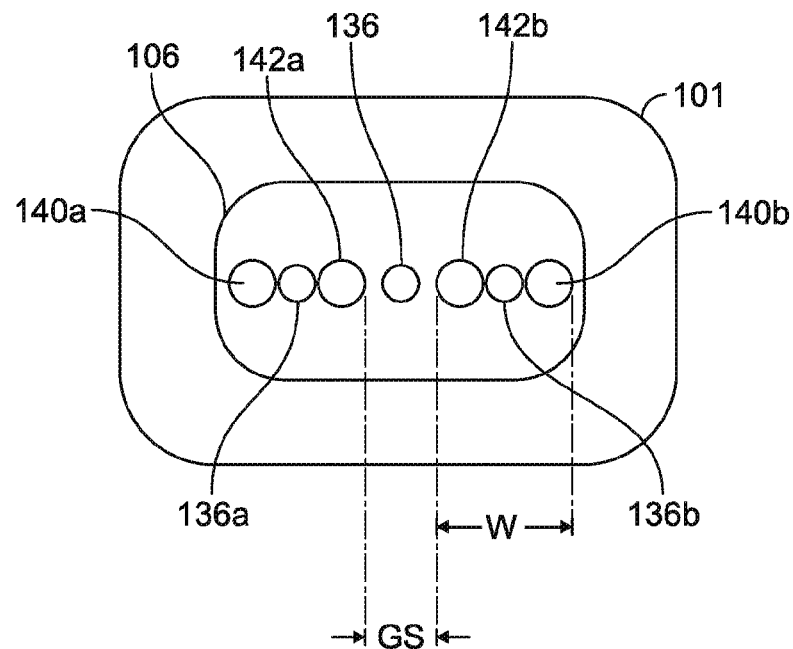
FIG. 10 is a close-up cross-sectional view of the electrodes of the device of FIG. 5. taken along line 10-10 of FIG. 5.

Alternatively, as shown in FIG. 8, fluid delivery tubing 16 may be inserted directly into receptacle 132 of shaft body 106. Fluid 12 then may flow through passage 134 before branching into passages 134a, 134b within shaft body 106 and being expelled from fluid delivery outlets 136a, 136b. Also, alternatively, a single fluid outlet 136 may be located between the electrodes 102a, 102b, as shown in FIG. 10, in which case outlets 136a, 136b may be omitted.

FIG. 9 provides a close-up view of shaft body 106, U-shaped electrodes 102a, 102b and fluid delivery outlets 136a, 136b. As shown, U-shaped electrodes 102a, 102b may be arranged to provide two fixed, laterally and spatially separated (by empty space) electrode tips which may be configured as mirror images in size and shape, and may have a blunt, rounded distal end which provides a smooth continuous surface (which is devoid of points or edges) to treat tissue. As shown, U-shaped electrodes 102a, 102b may be coplanar (i.e. in the same plane).

U-shaped electrodes 102a, 102b, which are adjacent the distal end 138 of shaft body 106, may each comprise lateral longitudinal segments 140a, 140b and medial longitudinal segments 142a, 142b which extend distally from the distal end 138 of shaft body 106 and are proximal to arcuate distal segments 144a, 144b. It should be understood that while the electrodes 102a, 102b have been described as having various segments, the description is aimed to provide orientation of such relative to the device, and not that the electrodes 102a, 102b are necessarily provided from separately formed individual segments which have been joined together. To the contrary, each electrode 102a, 102b may be particularly formed from a single continuous member, such as a single continuous piece of wire described in greater detail below.

As shown, the arcuate distal segments are continuously arcuate from one longitudinal segment to the other longitudinal segment without any interruptions, and more particularly may be semicircular with a radius of 180 degrees. Also as shown, fluid delivery outlet 136a is located between longitudinal segments 140a, 142a, and fluid delivery outlet 136b is located between longitudinal segments 140b, 142b. In this manner, fluid 12 expelled from fluid delivery outlets 136a, 136b may better form a fluid membrane between longitudinal segments 140a, 142a and 140b, 142b, respectively, as discussed in greater detail below.

Returning to FIG. 7, the lateral longitudinal segments 140a, 140b extend through the length of shaft body 106. However, the medial longitudinal segments 142a, 142b are retained in (e.g. interference/friction fit) and extend from receptacles (blind bores) 146a, 146b formed in the distal end of shaft body 106. As shown in the figures, lateral longitudinal segments 140a, 140b and medial longitudinal segments 142a, 142b are all parallel and coplanar (in the same plane).

In some embodiments, electrodes 102a, 102b may particularly be formed from single strand, metal (particularly stainless steel) wire. Each electrode 102a, 102b may have an overall (exposed) length L in the range of and any increment between 4 mm to 15 mm, and more particularly 6 mm to 12 mm. Each electrode 102a, 102b may have a width W in the range of and any increment between 1 mm to 4 mm, and more particularly 2 mm to 3 mm. In embodiments in which electrodes 102a, 102b are formed from round solid wire, forming tools, such as grinders or sanders, can be used to give electrodes 102a, 102b a desired cross-sectional shape.

In some embodiments, electrodes 102a, 102b may be formed from a flat sheet of material, for example, flat stainless steel stock. The desired cross-sectional shape of electrodes 102a, 102b can then be formed using manufacturing methods such as electro-diode machining, electro-chemical machining, or electro-chemical grinding. Using such manufacturing methods, electrodes 102a, 102b can be easily customized for an intended use of device 30.

As shown in FIG. 10, electrodes 102a, 102b may be cylindrical and have a circular cross-sectional profile with a cross-section thickness, here diameter, in a range of and any increment between 0.1 mm to 1.5 mm, and more particularly 0.5 mm to 1 mm, and even more particularly 0.6 to 0.75 mm.

With respect to spacing, the spatial gap separation GS between electrodes 102a, 102b may be in the range of and any increment between 0.1 mm to 3 mm, and more particularly 0.5 mm to 2 mm, and even more particularly 0.75 mm to 1.5 mm. The spacing between the medial 142a, 142b and lateral segments 140a, 140b of each electrode 102a, 102b may be in a range of and any increment between 0.1 mm to 3 mm, and more particularly 0.5 mm to 2 mm, and even more particularly 0.75 mm to 1.5 mm.

Figure 11:
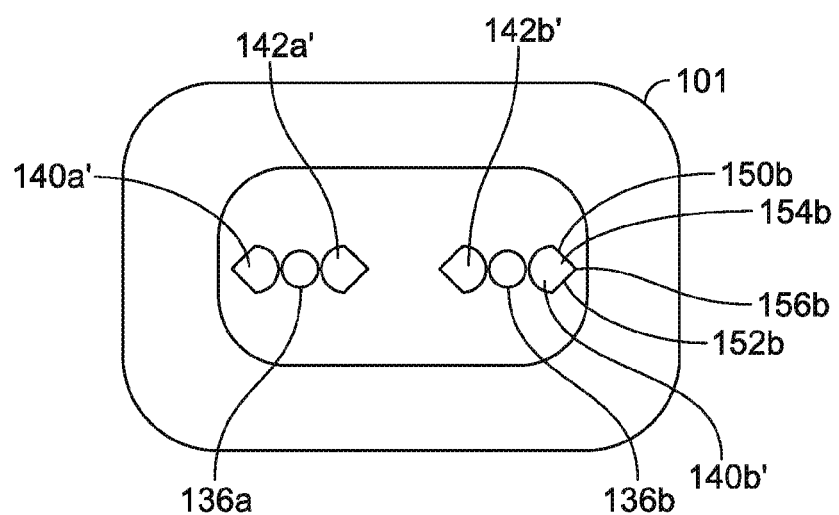
FIG. 11 is a close-up cross-sectional view of another embodiment of the electrodes of the device of FIG. 5 taken along line 10-10 of FIG. 5.

As shown in FIG. 11 at least a portion of the length of lateral longitudinal segment 140b' may be shaped, particularly from circular wire by grinding or sanding, as to have a cross-sectional profile with opposing sides 150b/152b which converge laterally to provide a wedge shaped blade portion 154b on the perimeter which terminates in a linear lateral cutting edge 156b which extends longitudinally along the length of longitudinal segment 140b'. As shown, in alternative embodiments, any of the remaining longitudinal segments 140a', 142a' or 142b' may have the same cross-sectional profile as segment 140b'.

As shown in FIG. 11, blade portion 154b narrows as the opposing sides 150b/152b approach cutting edge 156b. More particularly, the sides 150b/152b of blade portion 154b are planar. However, in other embodiments, sides 150b/152b may be concave or convex.

Figure 12:
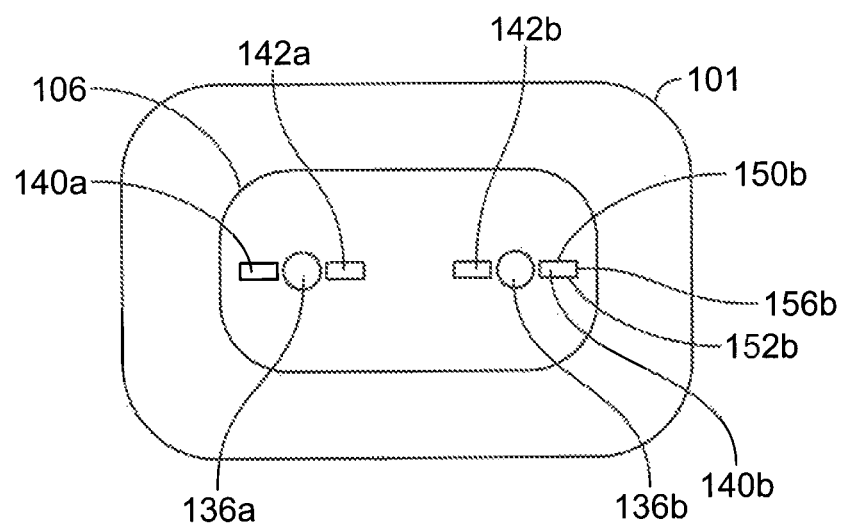
FIG. 12 is a close-up cross-sectional view of another embodiment of the 10 electrodes of the device of FIG. 5 taken along line 10-10 of FIG. 5.

As shown in FIG. 12, at least a portion of the length of lateral longitudinal segment 140b may be shaped, particularly from circular wire by grinding or sanding, as to have a profile with opposing sides 150b/152b which are substantially parallel and terminate at linear lateral cutting edge 156b which extends longitudinally along the length of longitudinal segment 140b. As shown, in alternative embodiments, any of the remaining longitudinal segments 140a, 142a, or 142b may have the same profile as segment 140b. Here, segment 140 has a polygonal profile, and more particularly a rectangular profile.

Figure 13:
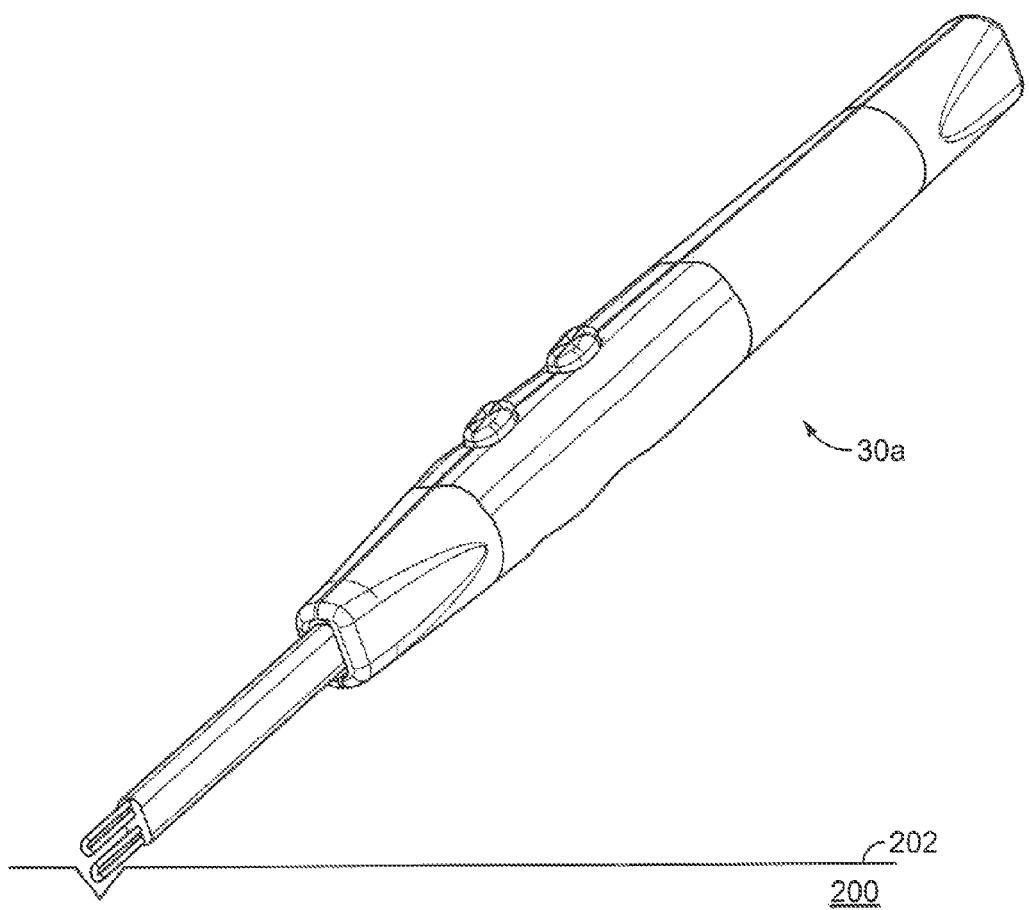
FIG. 13 is a perspective view of the device of FIG. 5 cutting tissue.

For the electrodes 102a, 102b shown in FIGS. 11 and 12, lateral cutting edge 156b may be particularly configured to cut tissue electrosurgically in the presence of monopolar radio frequency energy from electrosurgical unit 10 as to provide an electrosurgical cutting edge, but without any fluid 12 being provided from fluid source 20. However, in other embodiments, lateral cutting edge 156b may be configured to cut tissue with fluid 12 being provided simultaneously from device 30a, or be configured to cut tissue mechanically (sharpened) without electrosurgical energy. Referring now to FIG. 13, device 30a may be used to cut tissue by applying cutting edge 156b of electrode 102b to tissue 200, and repeatedly moving the electrode 102b along a desired incision or resection line in the tissue to form the depicted crevice.

While cutting edge 156b may be particularly configured to cut tissue with monopolar RF energy and without fluid 12 being expelled from device 30a, arcuate distal end segments 144a, 144b may be particularly configured to slide or otherwise move across a tissue surface in the presence of bipolar radio frequency energy from electrosurgical unit 10 and fluid 12 from the fluid source 20.

Figure 14:
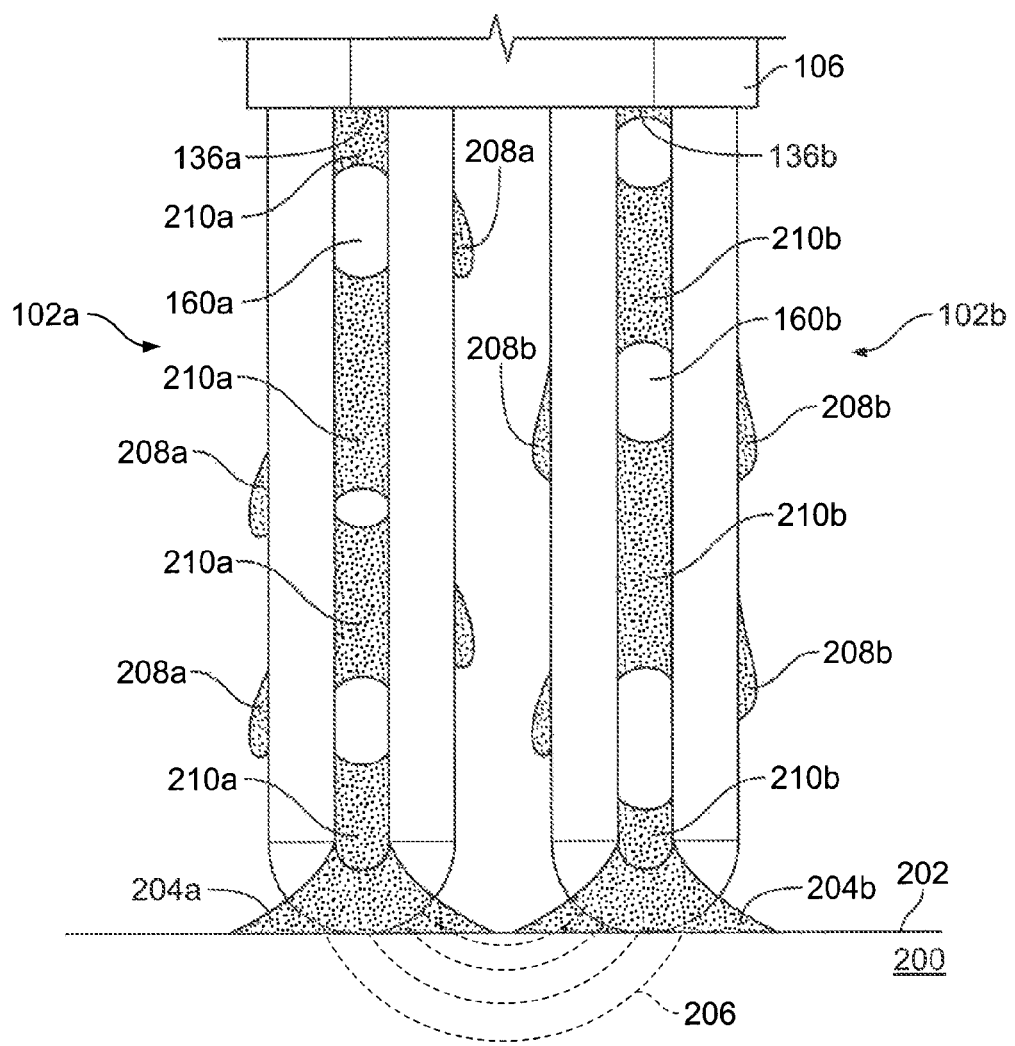
FIG. 14 is a close-up view of a distal end portion of the device of FIG. 5 with an exemplary fluid coupling to a tissue surface of tissue.
Figure 15:
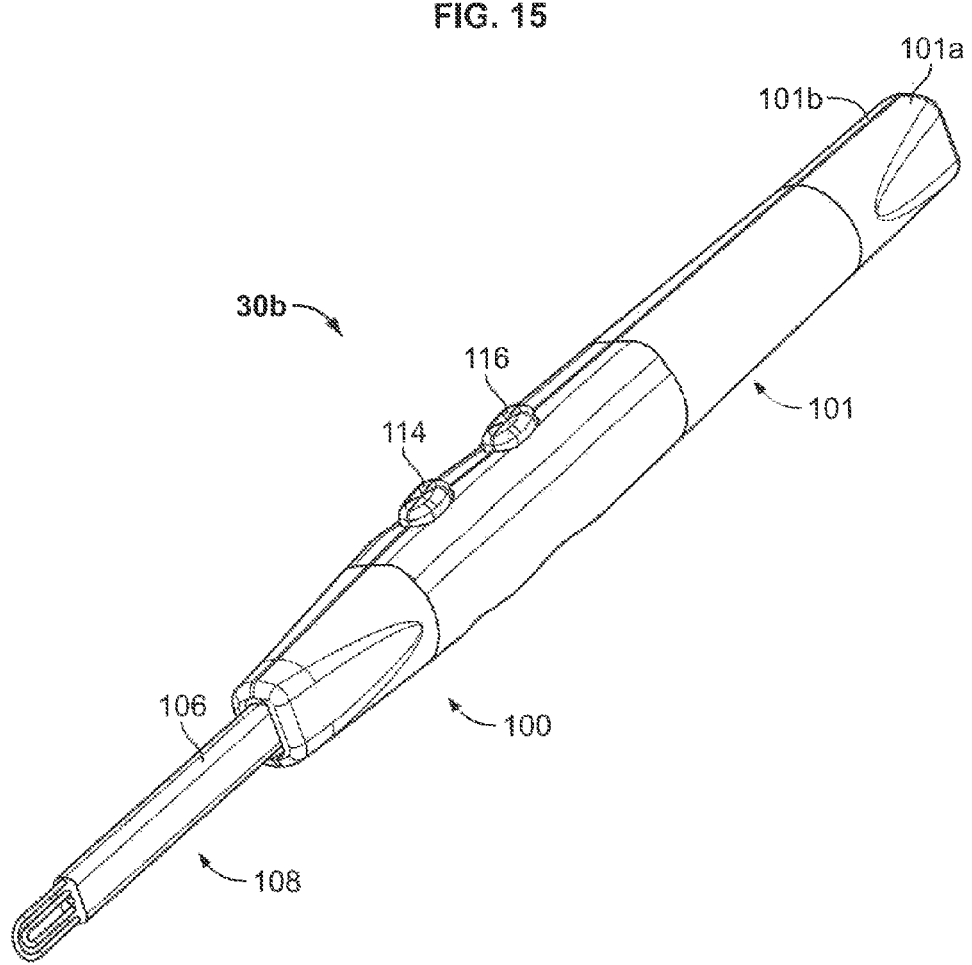
FIG. 15 is a perspective view of another embodiment of an electrosurgical device according to the present invention.
Figure 16:
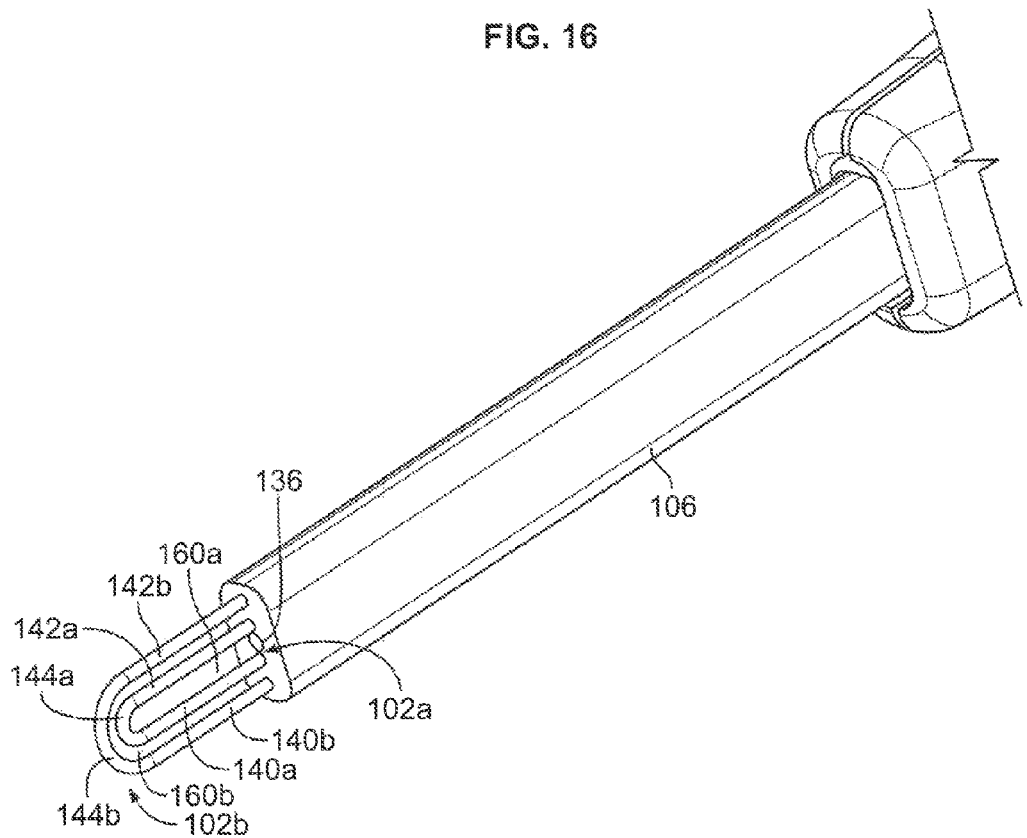
FIG. 16 is a close-up view of the shaft of the device of FIG. 15.
Figure 17:
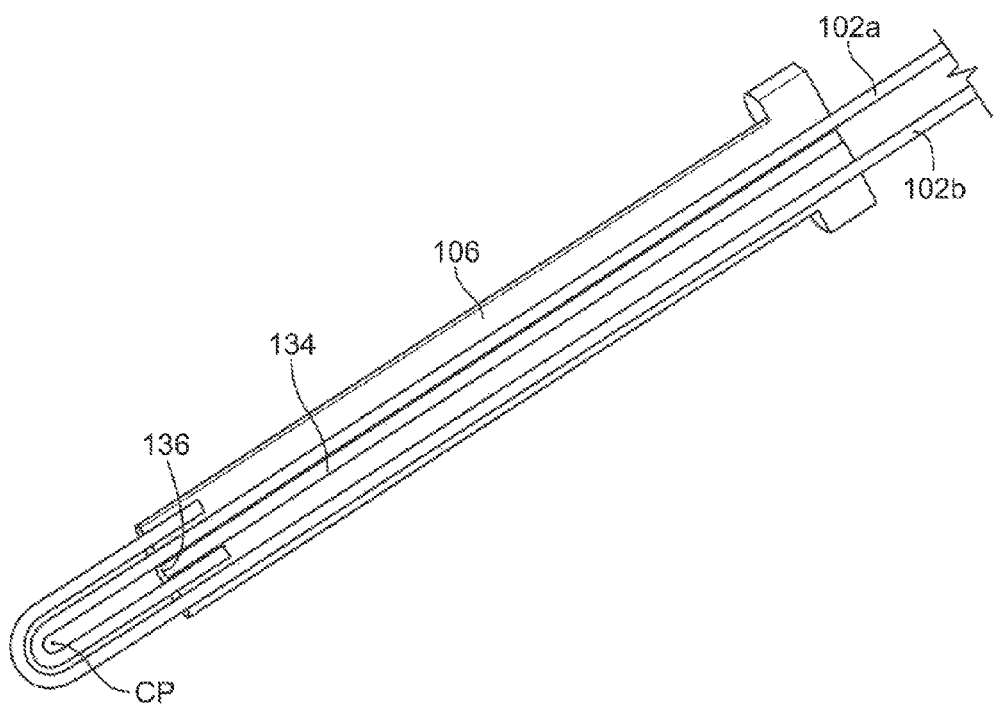
FIG. 17 is a close-up longitudinal cross-sectional view of the shaft of the device of FIG. 15.

As shown in FIG. 14, one way in which device 30a may be used as a bipolar device is with the longitudinal axis of electrodes 102a, 102b vertically orientated, and the arcuate distal segments 144a, 144b of electrodes 102a, 102b laterally spaced adjacent tissue surface 202 of tissue 200. When device 30a is used in this manner, electrodes 102a, 102b may be connected to electrosurgical unit 10 and receive bipolar radio frequency energy which forms an alternating current electrical field in tissue 200 located between electrodes 102a, 102b. In the presence of alternating current, the electrodes 102a, 102b alternate polarity between positive and negative charges with current flow from the positive to negative charge. Without being bound to a particular theory, heating of the tissue is performed by electrical resistance heating.

Fluid 12, in addition to providing an electrical coupling between the device 30a and tissue 200, lubricates surface 202 of tissue 200 and facilitates the movement of electrodes 102a, 102b across surface 202 of tissue 200. During movement of electrodes 102a, 102b, electrodes 102a, 102b typically slide across the surface 202 of tissue 200. Typically the user of device 30a slides electrodes 102a, 102b across surface 202 of tissue 200 back and forth with a painting motion while using fluid 12 as, among other things, a lubricating coating. Preferably the thickness of the fluid 12 between the arcuate distal segments 144a, 144b of electrodes 102a, 102b and surface 202 of tissue 200 at the outer edge of couplings 204a, 204b is in the range of 0.05 mm to 1.5 mm. Also, in certain embodiments, the arcuate distal segments 144a, 144b of electrodes 102a, 102b may contact surface 202 of tissue 200 without any fluid 12 in between.

As shown in FIG. 14, fluid 12 expelled from fluid outlets 136a, 136b may flow distally on electrodes 102a, 102b in the form of droplets 208a, 208b or as a membrane 210a, 210b extending across the U-shaped apertures 160a, 160b and bridging between longitudinal segments 140a, 142a and 140b, 142b of electrodes 102a, 102b. As shown in FIG. 14, droplets 208a, 208b may form at varying times from fluid 12 expelled from fluid outlets 136a, 136b. Also, fluid 12 may be expelled in varying quantity from each of the fluid outlets 136a, 136b, depending on, for example, device orientation, pressure, flow rate, and varying fluid outlet sizes. With use of device 30a, the physical characteristics of the droplets 208a, 208b and the membranes 210a, 210b may also vary due to changes in the surface finish of the electrodes 102a, 102b. For example, the membranes 210a, 210b may form a meniscus type curvature at either end thereof as they progress distally along electrodes 102a, 102b.

Fluid 12 in the form of membranes 210a, 210b bridging apertures 160a, 160b may offer certain advantages over droplets 208, 208b as the membranes 210a, 210b, after flowing distally along the longitudinal segments of electrodes 102a, 102b, may be more evenly distributed over arcuate distal segments 144a, 144b of electrodes 102a, 102b, to then form fluid couplings 204a, 204b. Also, membranes 210a, 210b may exhibit better retention to electrodes 102a, 102b while flowing distally along electrodes 102a, 102b and not fall off as may be the situation for droplets 208a, 208b.

As shown in FIG. 14, fluid couplings 204a, 204b may particularly comprise discrete, localized webs and more specifically comprise triangular shaped webs of fluid 12 between surface 202 of tissue 200 and electrodes 102a, 102b. When the user of electrosurgical device 30a places electrodes 102a, 102b at a tissue treatment site and moves electrodes 102a, 102b across the surface 202 of the tissue 200, fluid 12 is expelled from fluid outlets 136a, 136b around the surfaces of electrodes 102a, 102b and onto the surface 202 of the tissue 200 via couplings 204a, 204b. At the same time, RF electrical energy, shown by electrical field lines 206, is provided to tissue 200 at tissue surface 202 and below tissue surface 202 into tissue 200 through fluid couplings 204a, 204b. In the foregoing manner, device 30a may be used to seal tissue against blood and other fluid loss.

Thus, while cutting edge 156b may be particularly configured to cut tissue with monopolar RF energy and without fluid 12 being expelled from device 30a, arcuate distal end segments 144a, 144b may be particularly configured to slide or otherwise move across a tissue surface in the presence of bipolar radio frequency energy from electrosurgical unit 10 and fluid 12 from the fluid source 20.

Another embodiment of device 30 is shown in FIGS. 15-18 as device 30b. As shown, rather the U-shaped electrodes being spaced side-by-side as with embodiment 30a, the U-shaped electrodes are arranged such that the perimeter of U-shaped electrode 102a is surrounded by U-shaped electrode 102b, with U-shaped electrode 102a located within the U-shaped aperture 160b defined by electrode 102b. In this manner, the two longitudinal segments 140a, 142a of electrode 102a are now medial to the two longitudinal segments 140b, 142b of electrode 102b. Vice-versa, the two longitudinal segments 140b, 142b of electrode 102b are now lateral to the two longitudinal segments 140a, 142a of electrode 102a. As compared with device 30a, the electrode configuration of device 30b may be somewhat narrower, which may make device 30b less intrusive than device 30a and afford device 30b greater access to more confined locations with greater visibility.

As shown arcuate distal segments 144a, 144b of electrodes 102a, 102b may be concentric. In other words, arcuate distal segments 144a, 144b may have a common center point CP. As shown, similar to embodiment 30a, U-shaped electrodes 102a, 102b are coplanar (in the same plane). Also similar to embodiment 30a, longitudinal segments 140a, 140b and longitudinal segments 142a, 142b are all parallel and coplanar (in the same plane). Also similar to embodiment 30a, U-shaped electrodes 102a, 102b may have the same cross-sectional profiles as set forth in FIGS. 10-12. In this manner, electrode 102b may still include cutting edge 156b particularly configured to cut tissue with monopolar RF energy and without fluid 12 being expelled from device 30b.

Figure 18:
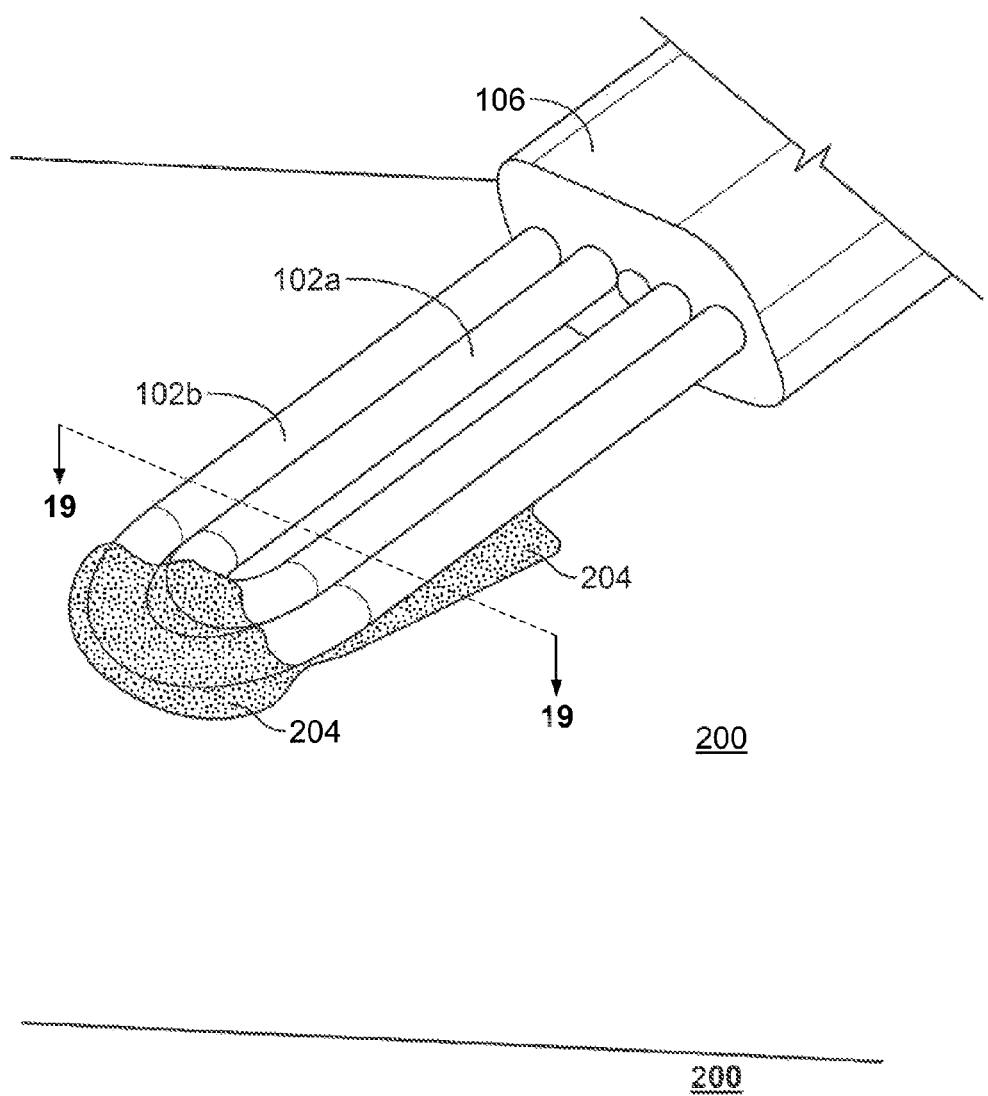
FIG. 18 is a close-up view of the electrodes of the device of FIG. 15 with an exemplary fluid coupling to a tissue surface of tissue.
Figure 19:
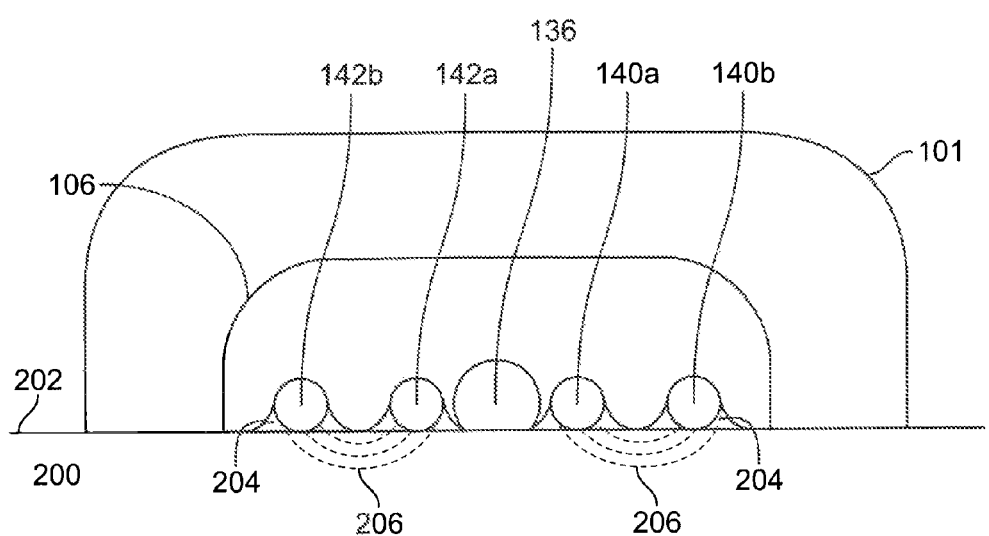
FIG. 19 is a close-up cross-sectional view of the device of FIG. 15 taken along line 19-19 with another view of a fluid coupling to a tissue surface of tissue.

As shown in FIGS. 18-19, one way in which device 30b may be used as a bipolar device is with the longitudinal axis of electrodes 102a, 102b substantially horizontally orientated. When device 30a is used in this manner, electrodes 102a, 102b may be connected to electrosurgical unit 10 and receive bipolar radio frequency energy which forms an alternating current electrical field in tissue 200 located between electrodes 102a, 102b and fluid 12 provided from device 30b.

Fluid 12, in addition to providing an electrical coupling between the device 30a and tissue 200, lubricates surface 202 of tissue 200 and facilitates the movement of electrodes 102a, 102b across surface 202 of tissue 200. As shown in FIGS. 18-19, fluid 12 expelled from fluid outlet 136 may form fluid couplings 204.

As shown in FIG. 19, fluid couplings 204 may particularly comprise localized webs and more specifically comprise triangular shaped webs of fluid 12 between surface 202 of tissue 200 and electrodes 102a, 102b. When the user of electrosurgical device 30b places electrodes 102a, 102b at a tissue treatment site and moves electrodes 102a, 102b across the surface 202 of the tissue 200, fluid 12 is expelled from fluid outlet 136 around the surfaces of electrodes 102a, 102b and onto the surface 202 of the tissue 200 via couplings 204. At the same time, RF electrical energy, shown by electrical field lines 206, is provided to tissue 200 at tissue surface 202 and below tissue surface 202 into tissue 200 through fluid couplings 204. In the foregoing manner, device 30b may be used to seal tissue against blood and other fluid loss.

Figure 20:
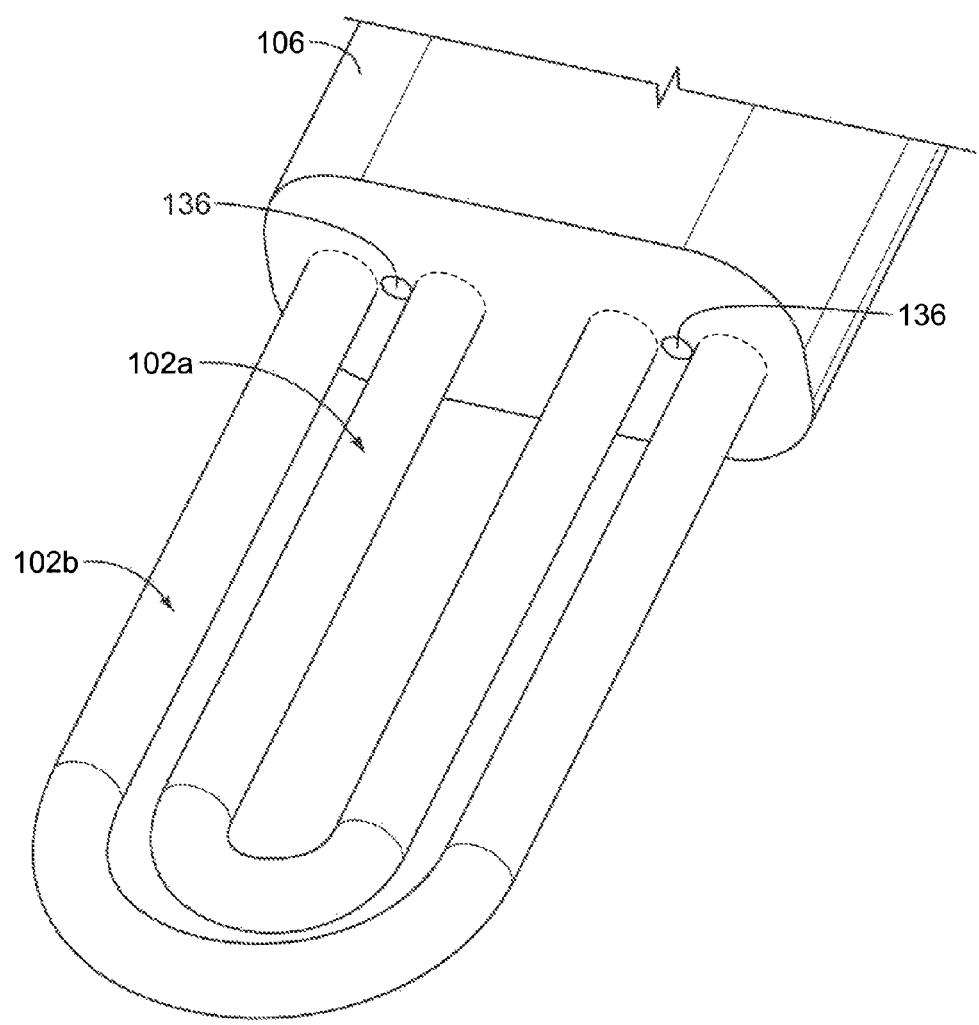
FIG. 20 is a close-up view of another embodiment of the fluid outlet(s) of the device of FIG. 15.

As shown in FIGS. 15-19, fluid outlet 136 may be located between longitudinal segments 140a, 142a of electrodes 102a. As shown in FIG. 20, a fluid outlet 136 may be located between longitudinal segments 142a of electrode 102a and longitudinal segment 142b of electrode 102b. A fluid outlet 136 may also be located between longitudinal segments 140a of electrode 102a and longitudinal segment 140b of electrode 102b. In various embodiments, any fluid outlet 136 may be used individually or in combination with any other of fluid outlet(s) 136 as shown. For example, one or both of the fluid outlets 136 shown in FIG. 20 may be used in combination with the fluid outlet 136 shown in FIGS. 15-19.

Figure 21:
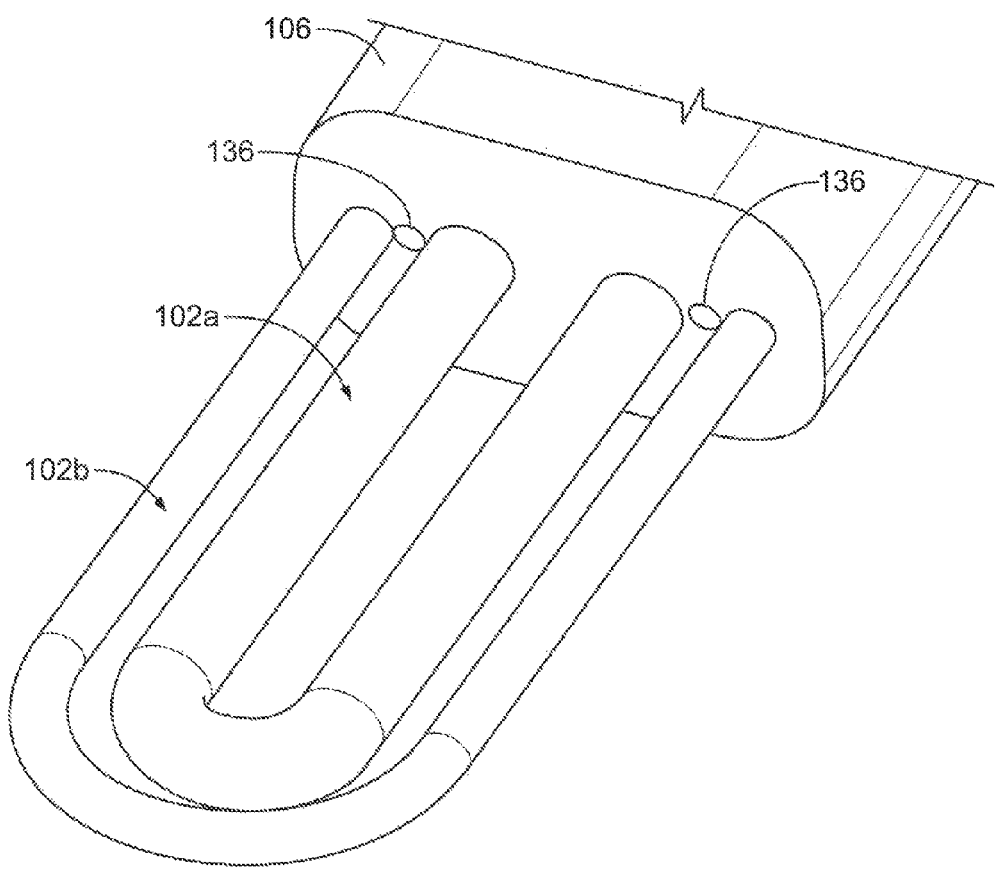
FIG. 21 is a is a close-up view of another embodiment of the electrodes of the device of FIG. 15.

For the embodiment of device 30b shown in FIGS. 15-19, outer electrode 102b has the same cross-sectional profile with a thickness (here diameter) equal to the diameter of inner electrode 102a. However, as shown in FIG. 21, outer electrode 102b may have a smaller cross-sectional profile with a thickness (here diameter) less than that of inner electrode 102a, to better facilitate cutting with a narrower incision, as well as better conforming to the tissue surface during sealing tissue, particularly by deforming when a slight pressure is applied by the user.

Figure 22:
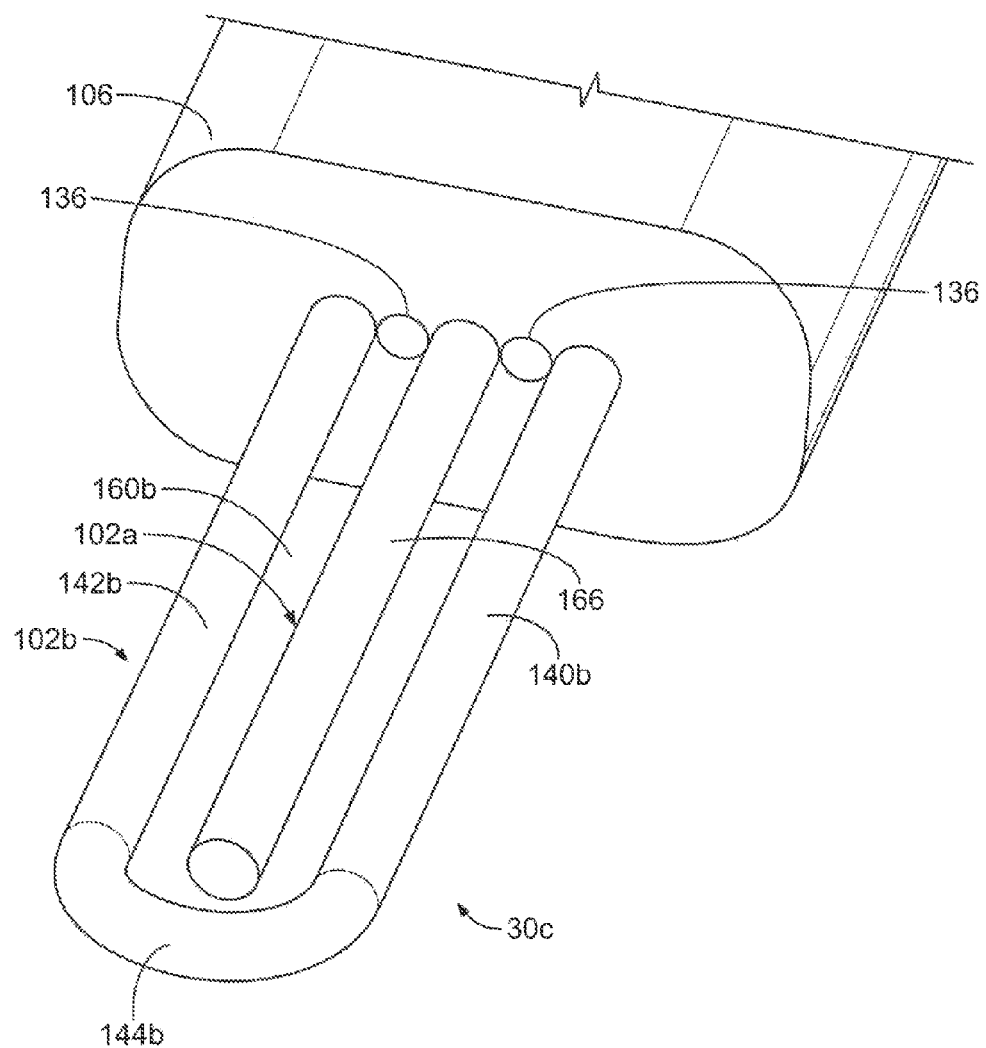
FIG. 22 is a perspective view of a distal portion of another embodiment of an electrosurgical device according to the present invention.

In another embodiment of the device 30, shown as device 30c in FIG. 22, electrode 102a may comprise a single longitudinal segment 166 rather than having a U-shape. Similar to device 30b, the perimeter of electrode 102a is surrounded by U-shaped electrode 102b, with electrode 102a located within the U-shaped aperture 160b defined by electrode 102b. In this manner, the longitudinal segment 166 of electrode 102a is medial to the two longitudinal segments 140b, 142b of electrode 102b. Vice-versa, the two longitudinal segments 140b, 142b of electrode 102b are lateral to longitudinal segment 166 of electrode 102a. As compared with device 30b, the electrode configuration of device 30c may be somewhat narrower, which may make device 30c less intrusive than device 30b and afford device 30c greater access to more confined locations with greater visibility.

As shown, similar to embodiments 30a and 30b, electrodes 102a, 102b are coplanar (in the same plane). Also similar to embodiments 30a and 30b, longitudinal segment 166 and longitudinal segments 142a, 142b are all parallel and coplanar (in the same plane). Also similar to embodiments 30a and 30b, electrodes 102a, 102b may have the same cross-sectional profiles as set forth in FIGS. 10-12. In this manner, electrode 102b may still include cutting edge 156b particularly configured to cut tissue with monopolar RF energy and without fluid 12 being expelled from device 30c.

Figure 23:
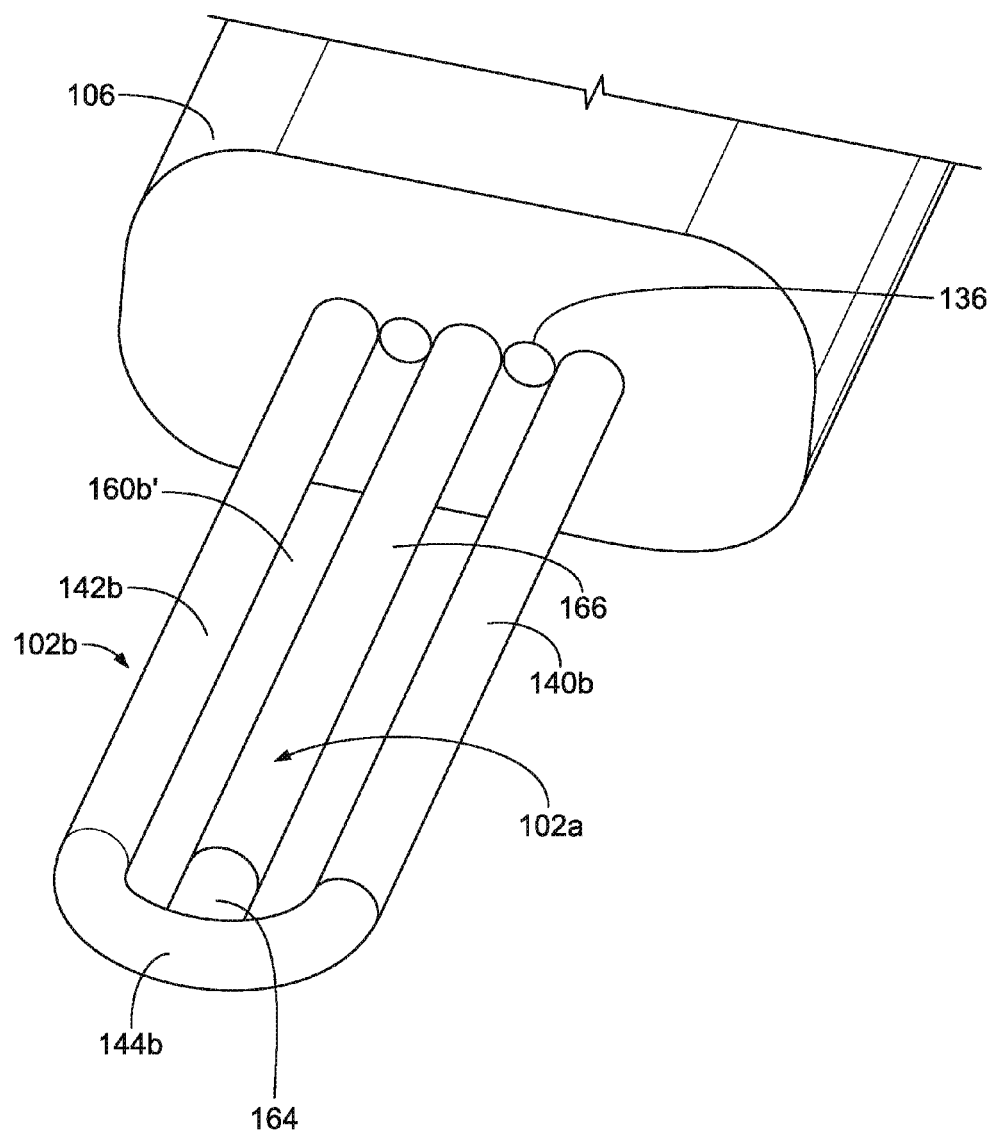
FIG. 23 is a perspective view of a distal portion of another embodiment of the electrosurgical device of FIG. 22 according to the present invention.

As, shown in FIG. 22, a fluid outlet 136 may be located between longitudinal segment 166 of electrode 102a and longitudinal segment 142b of electrode 102b. A fluid outlet 136 may also be located between longitudinal segment 166 of electrode 102a and longitudinal segment 140b of electrode 102b. Device 30c may be used similar to device 30b to cut and seal tissue as described herein. In an alternative embodiment, as shown in FIG. 23, an electrical insulator 164, such as formed from a synthetic polymer acetal), may be located between the two electrodes 102a, 102b, and particularly between the distal end of electrode 102a and the arcuate segment 144b of electrode 102b to better hold the position of the electrodes 102a, 102b relative to one another. Aperture 160b' is also shown.

Figure 24:
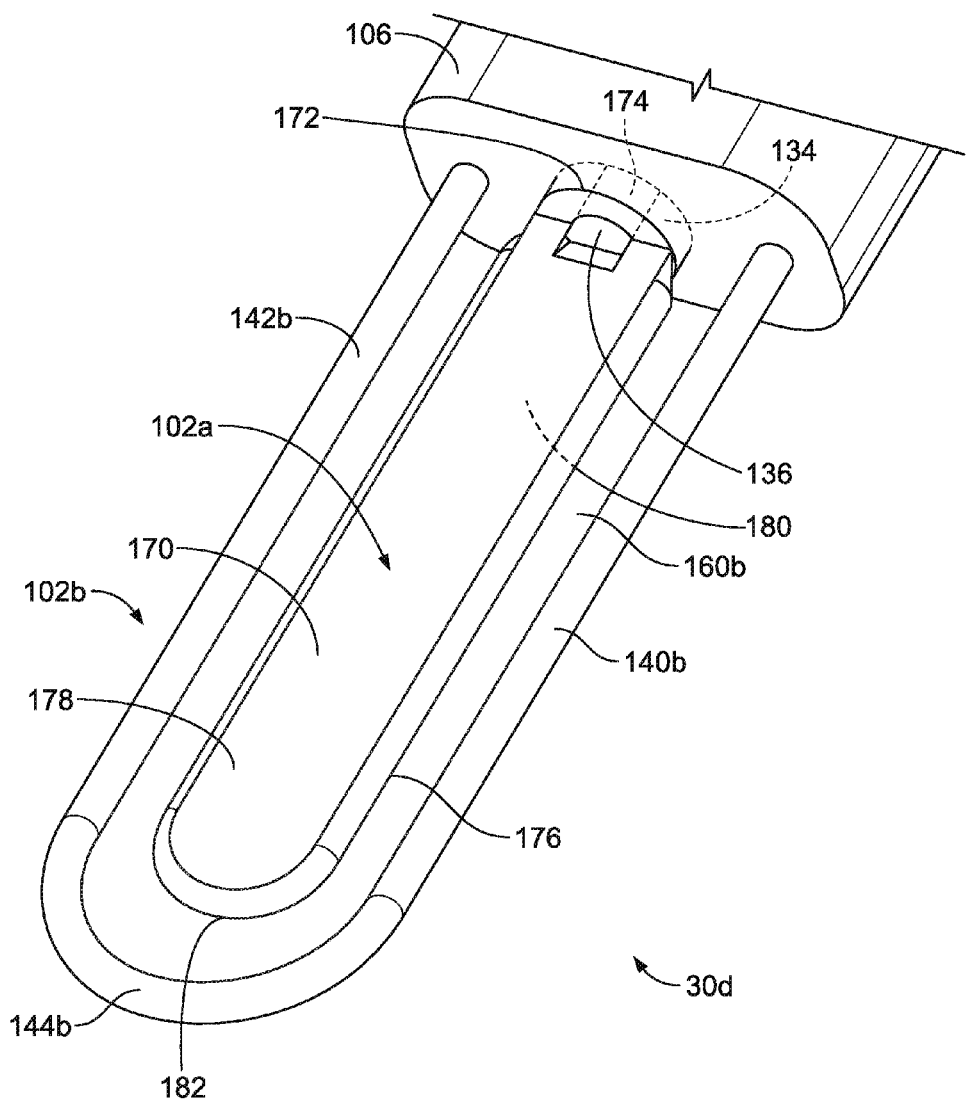
FIG. 24 is a perspective view of a distal portion of another embodiment of an electrosurgical device according to the present invention.

In another embodiment of the device 30, shown as device 30d in FIG. 24, electrode 102a may take the form of a longitudinally orientated elongated blade shaped member 170 with a planar body, such as may be provided by a flattened portion of metal (e.g., stainless steel) tubing 172 which has been inserted in tubular passage 134 of shaft body 106. In this manner, lumen 18 of fluid delivery tubing 16 may be in fluid communication with lumen 174 of metal tubing 172 such that fluid 12 may be expelled from fluid delivery outlet 136 adjacent the opposing sides 178, 180 of the blade member 170 as defined by the tubing 172, and insulated wire conductor 32c may be connected to a proximal portion of the tubing, particularly by welding. With regards to dimensions, in some embodiments, blade member 170 of electrode 102a may have a length in the range of and any increment between 4 mm to 15 mm, and more particularly 6 mm to 12 mm. In some embodiments, blade member 170 may have a width in the range of and any increment between 1 mm to 4 mm, and more particularly 2 mm to 3 mm. In some embodiments, blade member 170 can have a thickness between surface 178 and surface 180 in the range of about 0.1 to about 1.1 mm, and in some embodiments, is about 0.6 mm.

Similar to devices 30b and 30c, the perimeter of electrode 102a is surrounded by U-shaped electrode 102b, with electrode 102a located within the U-shaped aperture 160b defined by electrode 102b. In this manner, the blade member 170 of electrode 102a is medial to the two longitudinal segments 140b, 142b of electrode 102b. Vice-versa, the two longitudinal segments 140b, 142b of electrode 102b are lateral to blade member 170 of electrode 102a.

As shown, similar to embodiments 30a-30c, electrodes 102a, 102b are coplanar (in the same plane). Also similar to embodiments 30a-30c, blade member 170 and longitudinal segments 142a, 142b are all parallel and coplanar (in the same plane). Also similar to embodiments 30a-30c, electrode 102b may have the same cross-sectional profiles as set forth in FIGS. 10-12. In this manner, electrode 102b may still include cutting edge 156b particularly configured to cut tissue with monopolar RF energy and without fluid 12 being expelled from device 30d.

Figure 25:
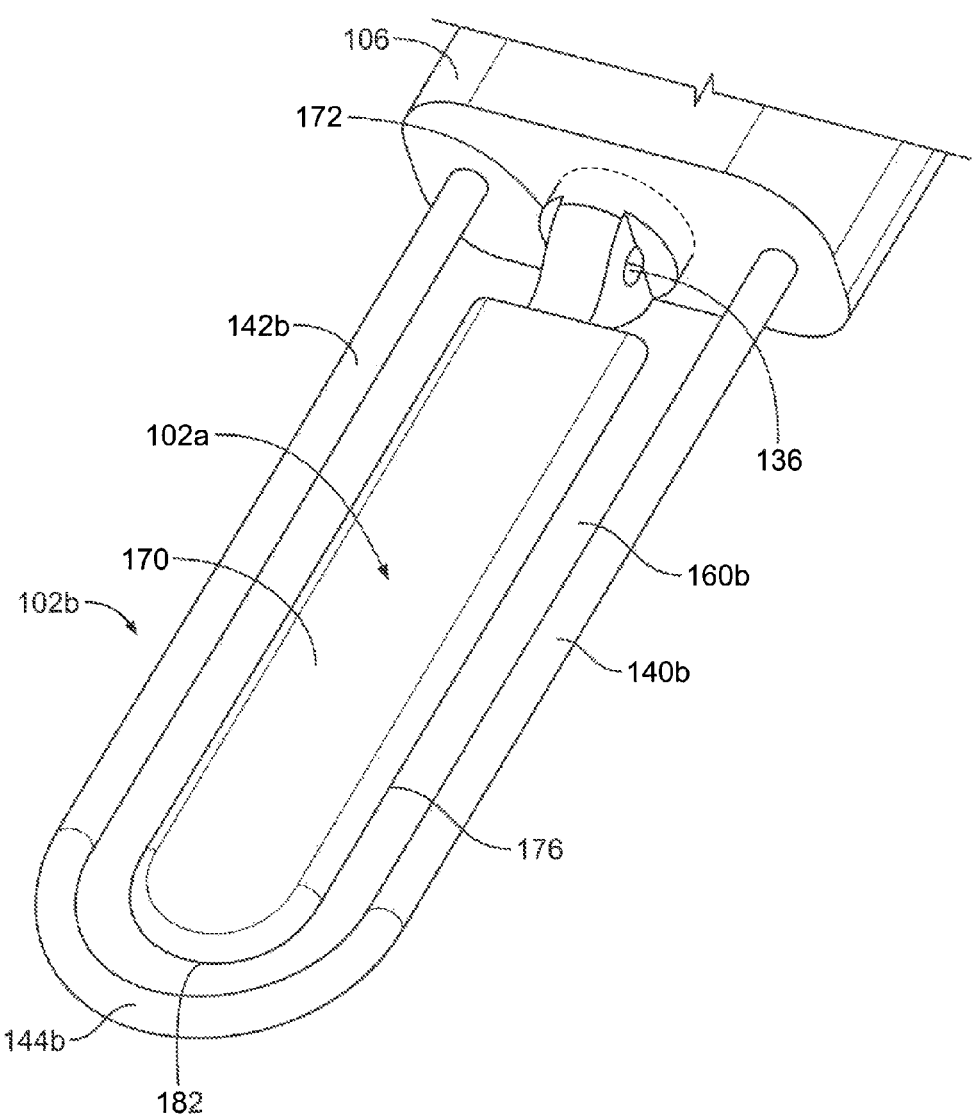
FIG. 25 is a perspective view of a distal portion of another embodiment of the electrosurgical device of FIG. 24 according to the present invention.

The perimeter 176 of blade member 170 from one (top) side 178 to the other (bottom) side 180 may be semi-circular as shown, or may have a narrow or pointed edge 156b as shown in either of FIG. 11 or 12. Also, as shown in FIG. 24, the distal end 182 of blade member 170 is arcuate, and more particular semi-circular, across the width of the blade member 170. Also as shown, the arcuate distal segment 144b of electrode 102b and the arcuate distal end 182 of blade member 170 may be concentric. As shown in FIG. 25, the fluid outlet 136 may be orientated parallel with the longitudinal perimeter of the blade member 170 to better feed fluid 12 directly into aperture 160b.

Figure 26:
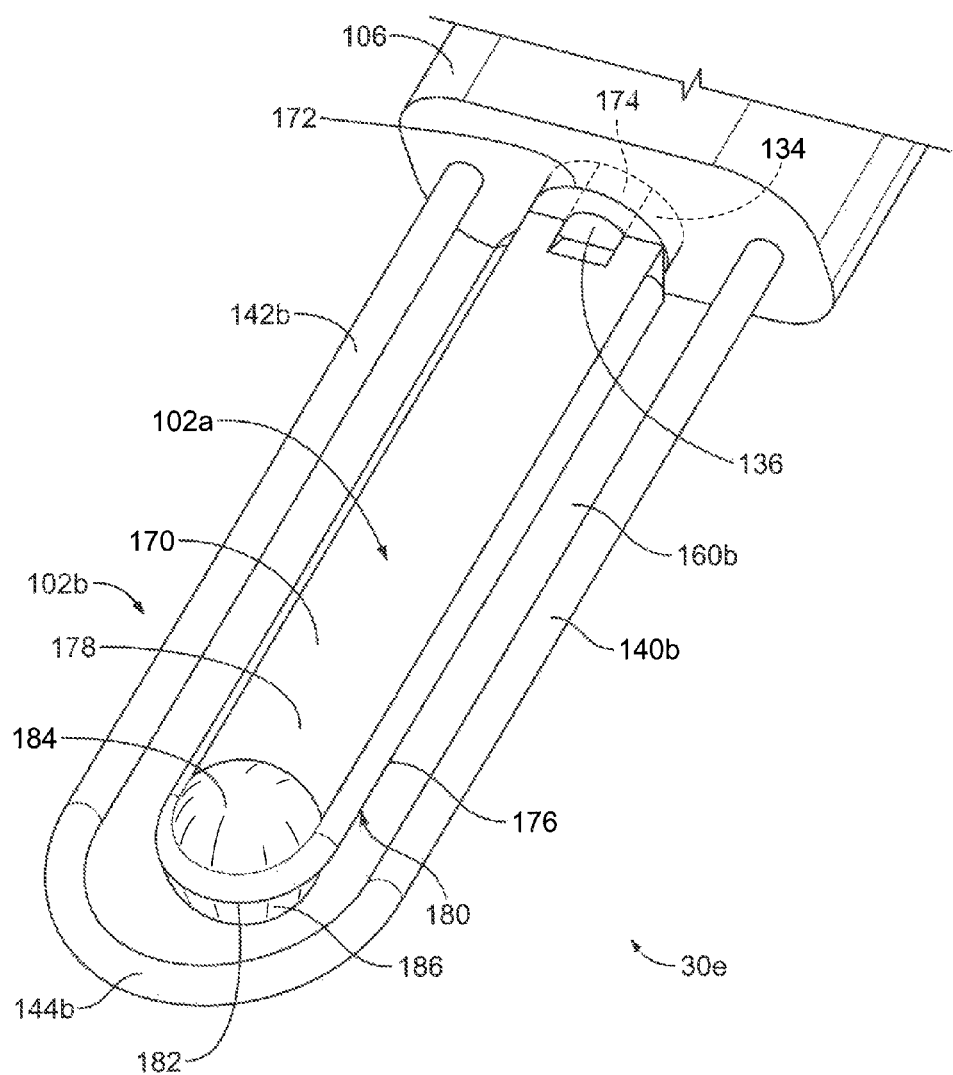
FIG. 26 is a perspective view of a distal portion of another embodiment of the electrosurgical device according to the present invention.

In another embodiment of the device 30, shown as device 30e in FIG. 26, blade member 170 can have a spherical distal end 182. As shown in FIG. 26, distal end 182 includes a first hemispherical surface 184 extending upward from side 178. Distal end 182 also includes a second hemispherical surface 186 extending downward from opposing side 180. Together first hemispherical surface 184 and second hemispherical surface 186 form a spherical surface at distal end 182. First and second hemispherical surfaces 184 and 186, forming spherical distal end 182, increase the surface area of electrode 102a in contact with tissue.

Figure 27:
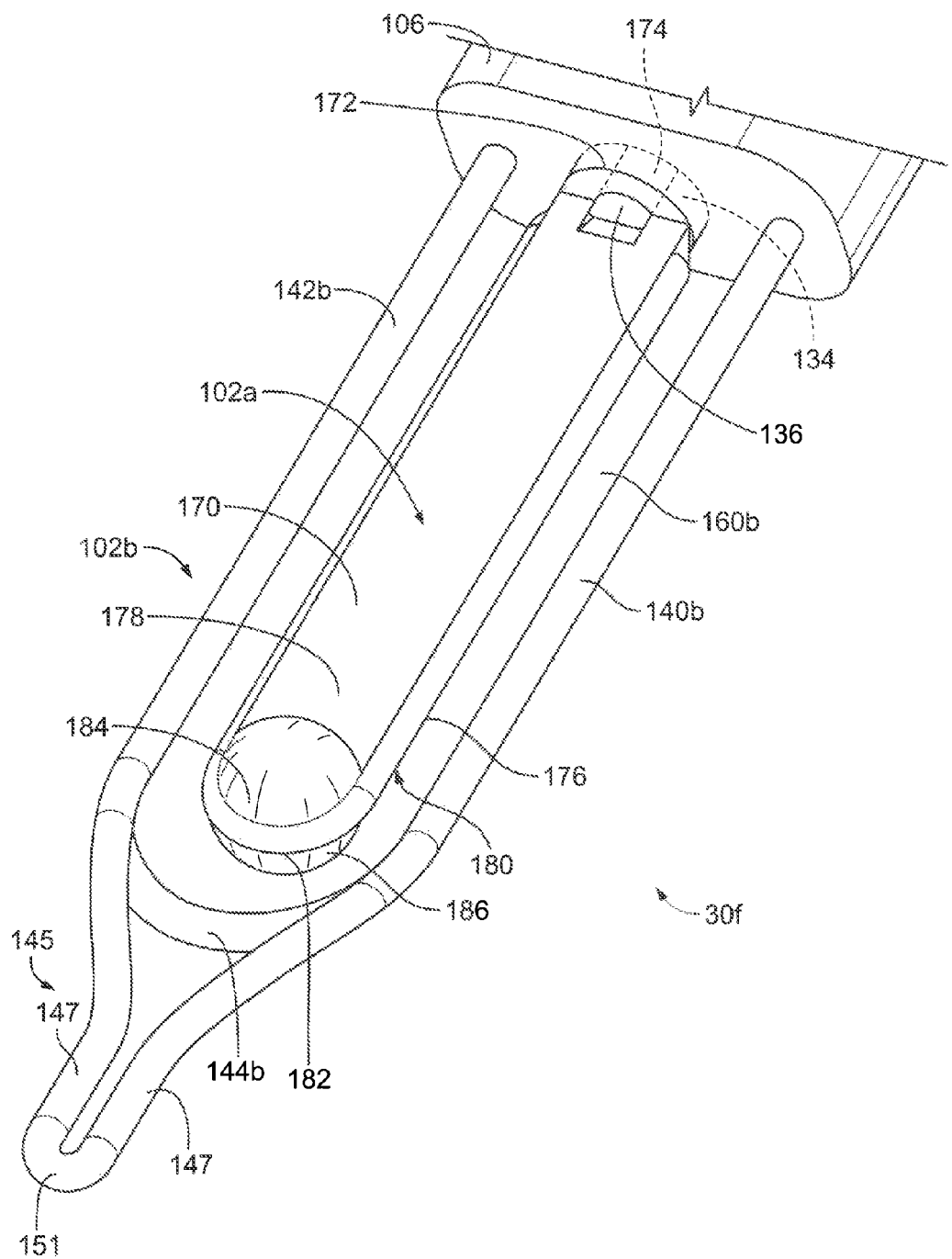
FIG. 27 is a perspective view of a distal portion of another embodiment of the electrosurgical device according to the present invention.

In other embodiments of the device 30, shown as devices 30f, 30g, 30h, and 30i in FIGS. 27-30, respectively, outer electrode 102b includes an electrically conductive pointed tip 145 or 145'. Particularly, in one embodiment as shown in FIG. 27, pointed tip 145 includes a pair of opposing longitudinal segments 147. Opposing longitudinal segments 147 extend distally from arcuate segment 144b. As opposing segments 147 extend away from arcuate segment 144b the space between segments 147 narrows. Opposing longitudinal segments 147 join together at arcuate segment 151. In one embodiment, as shown in FIG. 27, longitudinal segments 147 each have a concave shape. In one embodiment, the width between longitudinal segments 147 adjacent arcuate segment 151 is less than the width between longitudinal segments 140b and 142b. In some embodiments, the length of longitudinal segments 147 and arcuate segment 151 ranges from about 2.5 mm to about 7.5 mm, and in some embodiments, is about 5 mm.

Figure 28:
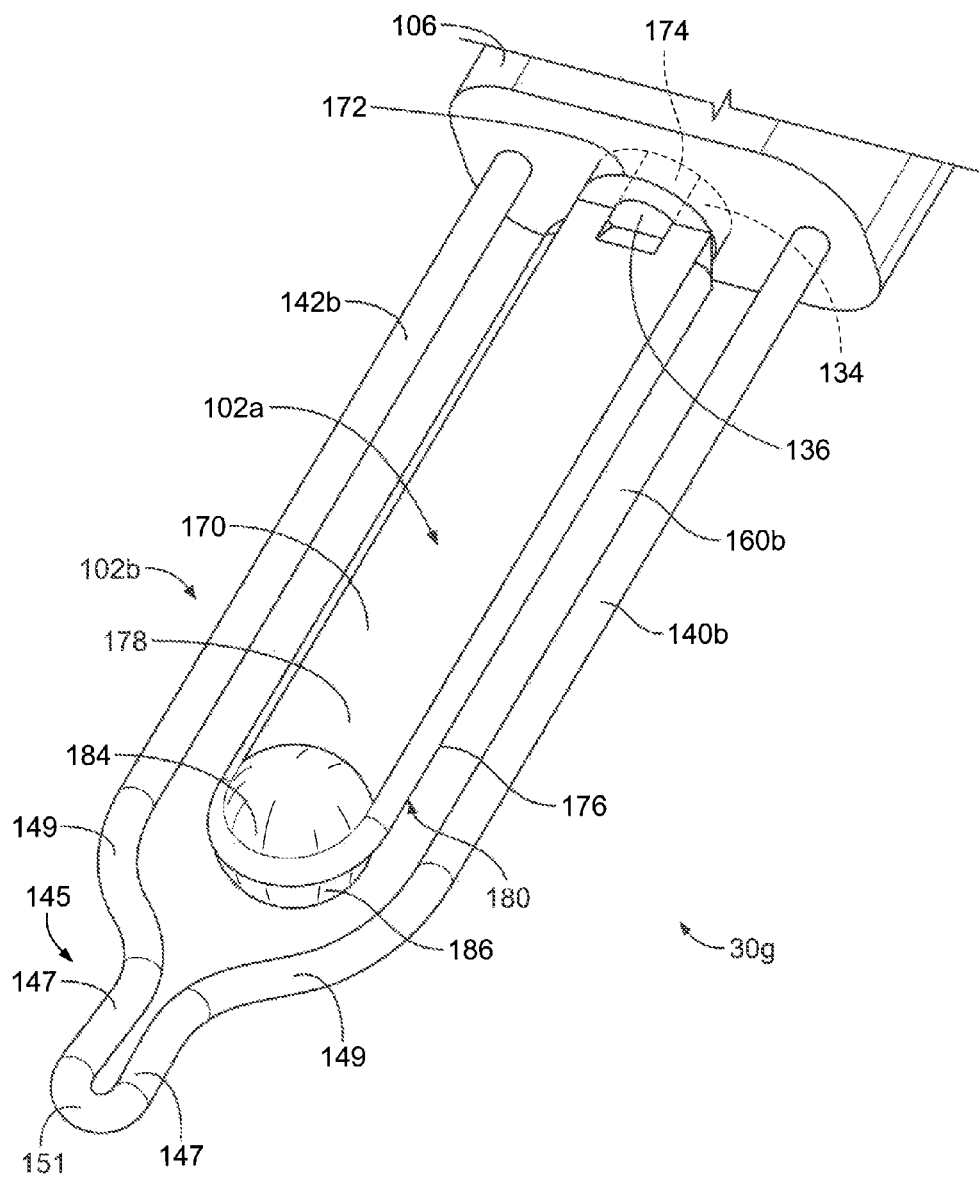
FIG. 28 is a perspective view of a distal portion of another embodiment of the electrosurgical device according to the present invention.

Another embodiment is shown in FIG. 28 as device 30g having pointed tip 145'. As shown, pointed tip 145' includes opposing longitudinal segments 147 joining together at arcuate segment 151, and a pair of opposing arcuate segments 149 extending from longitudinal segments 140b and 142b. In this embodiment, arcuate segments 149 curve inward around distal end 182 such that segments 149 are concentric with distal end 182. In one embodiment, longitudinal segments 147 extend distally from distal ends of arcuate segments 149 and join at arcuate segment 151. In some embodiments, longitudinal segments 147 have a length that ranges from about 2.5 mm to about 7.5 mm, and in some embodiments, is about 5 mm. In one embodiment, the width between longitudinal segments 147 is less than the width between longitudinal segments 140b and 142b, and is also less than the width of blade member 170, as illustrated in FIG. 28.

Figure 29:
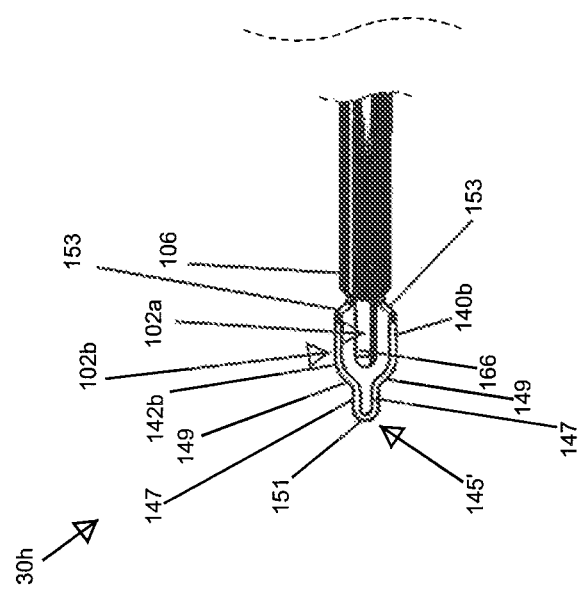
FIG. 29 is a plan view of a distal portion of the electrosurgical device according to another embodiment.

In some embodiments as shown in FIG. 29, a device 30h includes outer electrode 102b with pointed tip 145' and an inner electrode 102a that comprises longitudinal segment 166. Outer electrode 102b is shaped similar to the outer electrode 102b of device 30g except that outer electrode 102b of device 30h further includes a pair of opposing angled segments 153. Angled segments 153 are positioned between longitudinal segments 140b, 142b and shaft body 106. Each segment 153 extends from the distal end of shaft body 106 at an angle away from the longitudinal axis of shaft body 106.

Figure 30:
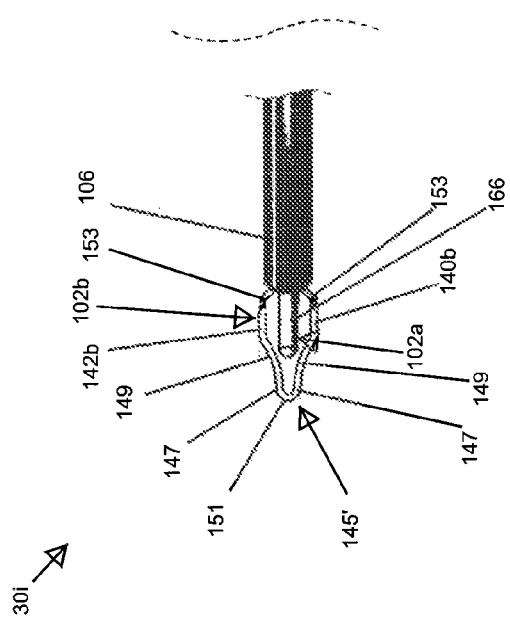
FIG. 30 is a plan view of a distal portion of the electrosurgical device according to another embodiment.

In some embodiments as shown in FIG. 30, a device 30i includes outer electrode 102b with pointed tip 145' and an inner electrode 102a that comprises longitudinal segment 166. Outer electrode 102b is shaped similar to the outer electrode 102 of device 30h except that arcuate segments 149 of device 30i are concave instead of convex as in device 30h shown in FIG. 29.

In some embodiments, pointed tips 145, 145' can have a length in a range from about 4 mm to about 5 mm, for example, about 4.6 mm, and a width in a range from about 3.5 mm to about 4.0 mm, for example, about 3.8 mm.

In some embodiments, outer electrode 102b can be configured to have a low-profile. For example, outer electrode 102b can have an overall width in a range of about 5 mm to about 6 mm, for example, about 5.6 mm, and a length in a range of about 9 mm to about 12 mm, for example, about 10.7 mm. In such embodiments, pointed tips 145, 145' can have a length in a range of about 3 mm to about 4 mm, for example, about 3.5 mm, and a width in a range of about 1.5 mm to about 2.5 mm, for example, about 2.0 mm.

Figure 31:
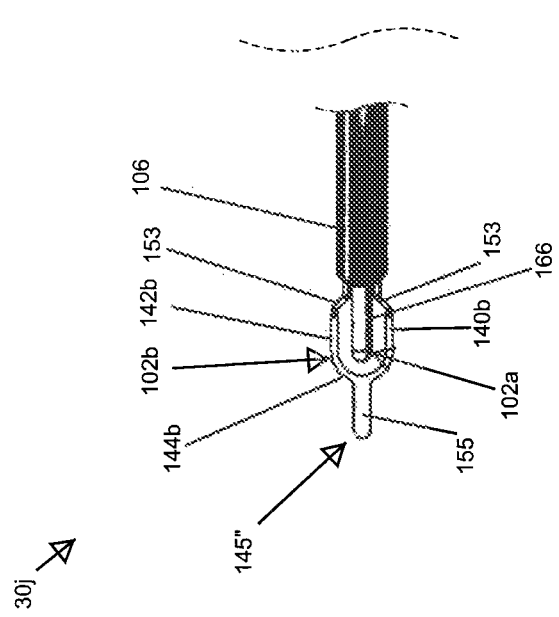
FIG. 31 is a plan view of a distal portion of the electrosurgical device according to another embodiment.
Figure 32:
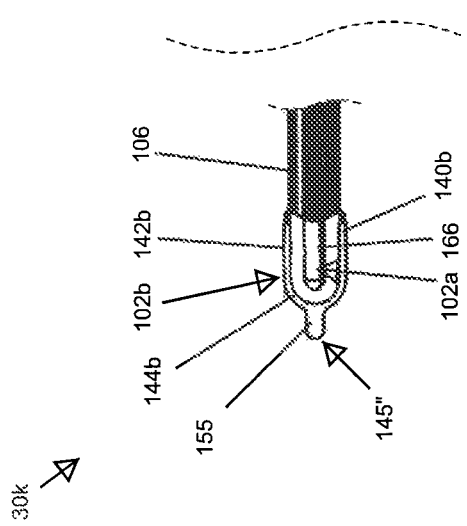
FIG. 32 is a plan view of a distal portion of the electrosurgical device according to another embodiment.
Figure 33:
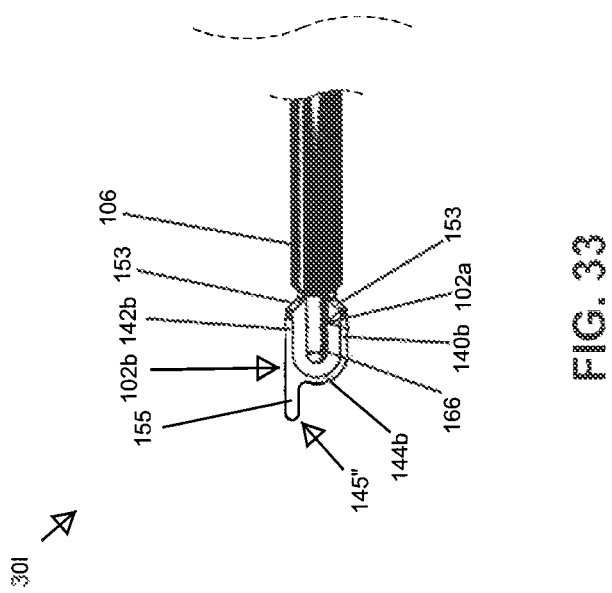
FIG. 33 is a plan view of a distal portion of the electrosurgical device according to another embodiment.

In some embodiments of the device 30, for example, devices 30j, 30k, and 30l shown in FIGS. 31, 32, and 33, respectively, outer electrode 102b includes an electrically conductive pointed tip 145" that is solid. Unlike pointed tips 145 and 145' shown in FIGS. 27-30 that comprise a plurality of segments that define a cavity there between, pointed tip 145" comprises a solid segment 155 that does not define a cavity. Solid segment 155 can have a rounded distal edge.

Solid segment 155 can extend distally from arcuate segment 144b. In some embodiments, solid segment 155 can extend from the center of arcuate segment 144b as in devices 30j and 30k shown in FIGS. 31 and 32. In such embodiments, solid segment 155 can be substantially coaxial with longitudinal segment 166 of inner electrode 102a and shaft body 106.

In some embodiments, solid segment 155 extends from an off-center position of arcuate segment 144b as shown, for example, in device 30l of FIG. 33. For example, in FIG. 33, solid segment 155 extends from a position adjacent longitudinal segment 142b. In such embodiments, solid segment 155 is not coaxial (i.e., it is eccentric) with longitudinal segment 166, and outer electrode 102b is asymmetric.

In some embodiments, solid segment 155 is substantially straight as shown in FIGS. 31-33. In some embodiments (not shown), solid segment 155 is curved or includes a plurality of straight segments that are angled relative to each other. In some embodiments, solid segment 155 has a cross-sectional shape as illustrated in FIGS. 10-12, or any other suitable cross-sectional shape. In some embodiments, solid segment 155 has a length that is about equal to the length of longitudinal segments 140b, 142b as shown, for example, in FIGS. 31 and 33. For example, in such embodiments, solid segment 155 can have a length in a range of about 7 mm to about 8 mm, for example, 7.5 mm, and a width in a range from about 2 mm to about 3 mm, for example, about 2.5 mm. In some embodiments, solid segment 155 has a length that is less the length of longitudinal segments 140b, 142b, for example, as shown in FIG. 32. For example, in such embodiments, solid segment 155 can have a length in a range from about 3 mm to about 4 mm, for example, about 3.5 mm, and a width in a range of about 2 mm to about 3 mm, for example, about 2.5 mm.

In some embodiments, solid segment 155 is formed integrally with longitudinal segments 140b, 142b and arcuate segment 144b. Alternatively, solid segment 155 can be formed separate from longitudinal segments 140b, 142b and arcuate segment 144b, and joined there to, for example, by welding.

In some embodiments, the width of pointed tip 145" and solid segment 155 is smaller than the width of pointed tips 145 and 145', which can improve visibility during surgery and minimize the area of the tissue being treated, allowing a user to "spot" treat a desired tissue area.

As compared to devices 30b and 30c, devices 30d, 30e, 30f, and 30g and particularly electrode 102b of each of these devices may be expected to cut tissue in a similar manner. In the embodiments including devices 30f and 30g illustrated in FIGS. 27 and 28, the narrow width of pointed tips 145 and 145' causes the energy to be more directed at tips 145 and 145' than around the remaining perimeter of electrode 102b, for example, longitudinal segments 140b and 142b, which allows for a finer precision cut, while still allowing cutting via the remaining perimeter of electrode 102b. Pointed tips 145 and 145' can also function as a spoon such that tissue mass can be scooped with pointed tips 145 and 145'. Pointed tips 145 and 145' can be used to puncture tissue.

With regards to sealing tissue, devices 30d-30l may be able to seal larger areas of tissue from blood and other fluid loss by having an increased surface area of electrode 102a as provided by blade member 170. In the embodiments 30e-30g, fluid outlet 136 can be oriented such as shown in FIG. 24 or as shown in FIG. 25, described above with reference to device 30d.

Device 30 and the various embodiments disclosed herein, such as 30a-30l, may be particularly useful to surgeons to achieve hemostasis after cutting through soft tissue, as part of hip or knee arthroplasty. The electrodes 102a, 102b of device 30 may be moved with a painting motion over the raw, oozing surface 202 of tissue 200 to seal the tissue 200 against bleeding, or focused on individual larger bleeding vessels to stop vessel bleeding. As part of the same or different procedure, device 30 may be useful to stop bleeding from the surface of cut bone, or osseous, tissue as part of any orthopaedic procedure that requires bone to be cut. Device 30 may be particularly useful for use during orthopedic knee, hip, shoulder and spine procedures. Additional discussion concerning such procedures may be found in U.S. Publication No. 2006/0149225, published Jul. 6, 2006, and U.S. Publication No. 2005/0090816, published Apr. 28, 2005, which are assigned to the assignee of the present invention and are hereby incorporated by reference in their entirety to the extent they are consistent.

Device 30, and the various embodiments disclosed herein, such as 30a-30l, may be particularly useful as non-coaptive devices that provide cutting of tissue, as well as coagulation, hemostasis and sealing of tissue to inhibit blood and other fluid loss during surgery. In other words, grasping of the tissue is not necessary to shrink, coagulate, cut and seal tissue against blood loss, for example, by shrinking collagen and associated lumens of blood vessels (e.g., arteries, veins) to provide the desired hemostasis of the tissue. Furthermore, due to the configuration of the electrodes, the electrodes may be easily bent by a user of the devices as needed. The electrodes may also be used for other functions, such as providing a spoon like platform for scooping of tissue (as earlier described with reference to the embodiments including devices 30f and 30l), such as an abnormal tissue mass (e.g. cancer). In some embodiments, the distal tips of electrodes 102a and 102b of devices 30a-30l can be bent up or configured to reduce the likelihood that the distal tips get caught on the tissue. The configurations of first and second electrodes 102a and 102b of the embodiments including devices 30b-30l can be used in either monopolar mode (e.g., for cutting) and bipolar mode (e.g., for tissue sealing). In monopolar mode, electrode 102b is used as the monopolar electrode for cutting, which can be performed on both sides of the electrode using a sweeping motion. Thus, electrode 102b of devices 30b-30l is not restricted to only one side of one electrode to achieve cutting. Moreover, when used in bipolar mode for tissue sealing, both electrodes 102a and 102b are in contact with the tissue and, in some embodiments, can be flexible to assure better contact for tissue sealing. Additionally, the embodiments described herein provide for improved visibility of the tissue being treated by the medical practitioner.

In some embodiments, including devices 30b-30l having co-planar electrodes 102a and 102b, electrodes 102a and 102b are configured to have minimal surface area and minimal mass. The reduction in surface area and mass can allow devices 30b-30g to operate cooler, faster, and with less thermal damage (e.g., by providing low power and having less thermal spread at the treated tissue site). In some embodiments, the shape set for electrode 102b can be configured to either maximize or minimize sealing, and configured to scoop or puncture tissue. In some embodiments, including devices 30b-30l, device 30 can be configured to be used in a 5 mm trocar.

Furthermore, the control system of the electrosurgical unit 10 is not necessarily dependent on tissue feedback such as temperature or impedance to operate. Thus, the control system of electrosurgical unit 10 may be open loop with respect to the tissue which simplifies use.

As established above, device 30 of the present invention inhibit such undesirable effects of tissue desiccation, electrode sticking, char formation and smoke generation, and thus do not suffer from the same drawbacks as prior art dry tip electrosurgical devices. The use of the disclosed devices can result in significantly lower blood loss during surgical procedures. Such a reduction in blood loss can reduce or eliminate the need for blood transfusions, and thus the cost and negative clinical consequences associated with blood transfusions, such as prolonged hospitalization.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner(s) in which the invention may be claimed, or that all recited features are necessary.

All publications and patent documents cited in this application are incorporated by reference in their entirety for all purposes to the extent they are consistent.

What is claimed is:

1. An electrosurgical device comprising:
   an elongate shaft having a longitudinal and axis and a distal end;
   a first U-shaped electrode at the distal end of the shaft, the first U-shaped electrode being substantially situated in a plane that is substantially parallel to the longitudinal axis of the shaft;
   a second electrode at the distal end of the shaft comprising a spherical distal end; and
   at least one fluid outlet, wherein the at least one fluid outlet is spaced said first electrode;
   the second electrode being substantially coplanar with the first electrode such that the first electrode surrounds a perimeter of the second electrode, and the second electrode being spaced from the first electrode by an aperture.

2. The device of claim 1, wherein the first electrode comprises a cutting edge.

3. The device of claim 1, wherein the first electrode is a wire electrode.

4. The device of claim 1, wherein the first electrode comprises an electrically conductive pointed tip at a distal end of the first electrode.

5. The device of claim 1, wherein the first electrode has a circular cross-section.

6. An electrosurgical device comprising:
   a shaft;
   a first electrode at a distal end of the shaft defining an aperture and comprising a penned tip;
   a second electrode disposed at the distal end of the shaft that is substantially coplanar with the first electrode such that the first electrode surrounds a perimeter of the second electrode, and the second electrode being spaced from the first electrode by the aperture,
   wherein the first electrode further comprises two longitudinal segments extending distally relative distal end of the shaft, and wherein the pointed tip extends from distal ends of the two longitudinal segments, and
   wherein the pointed tip comprises a pair of opposing arcuate segments extending from distal ends of the two first longitudinal segments and a pair of second longitudinal segment extending from distal ends of the pair of opposing arcuate segments, the pair of second longitudinal segments joining at a distal arcuate segment.

7. The electrosurgical device of claim 6, wherein the pair of opposing arcuate segments are concave.

8. The electrosurgical device of claim 6, wherein the second electrode is blade shaped.

9. The electrosurgical device of claim 6, wherein the second electrode comprises a spherical distal end.

10. The electrosurgical device of claim 6, further comprising at least one fluid outlet disposed adjacent the first and second electrodes for dispensing a fluid.

11. The electrosurgical device of claim 6, wherein the first electrode comprises a cutting edge.

12. The electrosurgical device of claim 6, wherein the first electrode is a wire electrode.

13. The electrosurgical device of claim 6, wherein the first electrode has a circular cross-section.

14. An electrosurgical device comprising:
    a shaft;
    a first electrode at a distal end of the shaft defining an aperture and comprising a pointed tip;
    a second electrode disposed at the distal end of the shaft that is substantially coplanar with the first electrode such that the first electrode surrounds a perimeter of the second electrode, and the second electrode being spaced from the first electrode by the aperture,
    wherein the first electrode further comprises two longitudinal segments extending distally relative to the distal end of the shaft and an arcuate segment joining the two longitudinal segments, and wherein the pointed tip comprises a solid segment extending distally from the arcuate segment,
    wherein the second electrode comprises a longitudinal segment, and
    wherein the solid segment extends from a center of the arcuate segment such that the solid segment is coaxial with the longitudinal segment of the second electrode.

15. An electrosurgical device comprising:
    a shaft;
    a first electrode at a distal end of the shaft defining an aperture and comprising a pointed tip;
    a second electrode disposed at the distal end of the shaft that is substantially coplanar with the first electrode such that the first electrode surrounds a perimeter of the second electrode, and the second electrode being spaced from the first electrode by an aperture,
    wherein the first electrode further comprises two longitudinal segments extending distally relative to the distal end of the shaft and an arcuate segment joining the two longitudinal segments, and wherein the pointed tip comprises a solid segment extending distally from the arcuate segment,
    wherein the second electrode comprises a longitudinal segment, and wherein the solid segment extends from a position offset from a center of the arcuate segment such that the solid segment is eccentric with the longitudinal segment of the second electrode.

* * * * *